United States Patent
Braeuer et al.

(10) Patent No.: US 7,375,098 B2
(45) Date of Patent: May 20, 2008

(54) 8β-VINYL-11β-(ω-SUBSTITUTED)ALKYL-ESTRA-1,3,5(10)-TRIENES

(75) Inventors: Nico Braeuer, Jena (DE); Olaf Peters, Tabarz (DE); Alexander Hillisch, Velbert (DE); Rolf Bohlmann, Berlin (DE); Margit Richter, Jena (DE); Hans-Peter Muhn, Berlin (DE)

(73) Assignee: Schering A.G., Berlin (DE)

( * ) Notice: Subject to any disclaimer, the term of this patent is extended or adjusted under 35 U.S.C. 154(b) by 580 days.

(21) Appl. No.: 10/829,390

(22) Filed: Apr. 22, 2004

(65) Prior Publication Data
US 2005/0065135 A1    Mar. 24, 2005

Related U.S. Application Data

(60) Provisional application No. 60/464,630, filed on Apr. 23, 2003.

(30) Foreign Application Priority Data
Apr. 22, 2003 (DE) ................ 103 18 896

(51) Int. Cl.
*A61K 31/56* (2006.01)
*A61K 31/58* (2006.01)
*C07J 1/00* (2006.01)

(52) U.S. Cl. .............. 514/182; 514/176; 552/626; 552/629

(58) Field of Classification Search ........ 552/626, 552/629; 514/176, 182
See application file for complete search history.

(56) References Cited

FOREIGN PATENT DOCUMENTS

DE   10151114   4/2003

WO   WO01/77138   10/2001

OTHER PUBLICATIONS

Lobaccaro C et al: "Steroidal Affinity Labels of the Estrogen Receptor 3, Estradiol 11.beta.-n-Alkyl Derivatives Bearing a Terminal Electrophilic Group: Anti-Estrogenic and Cytotoxic Properties" Journal of Medicinal Chemistry, American Chemical Society, Washington US, bd. 40, Nr. 14, Jul. 4, 1997.

*Primary Examiner*—Barbara P. Badio
(74) *Attorney, Agent, or Firm*—Millen, White, Zelano, Branigan, P.C.

(57) ABSTRACT

This invention relates to 8β-vinyl-11β-(ω-substituted)alkyl-estra-1,3,5(10)-trienes of general formula I

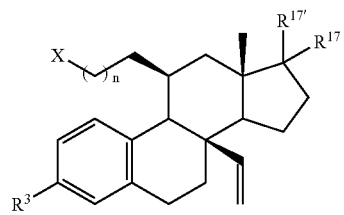

with ERβ-antagonistic activity, process for their production, their intermediate products, pharmaceutical preparations that contain the compounds according to the invention, as well as their use for the production of pharmaceutical agents.

The new compounds can be used for contraception in men and women without influencing other estrogen-sensitive organs such as the uterus or the liver.

They are also suitable for treating benign or malignant proliferative diseases of the ovary, such as ovarian cancer and granulosa cell tumors.

19 Claims, 8 Drawing Sheets

Figure 1 Synthesis scheme 1

Synthesis scheme 2

Synthesis scheme 3

Synthesis scheme 4

Synthesis scheme 5

Synthesis scheme 6

Synthesis scheme 7

Synthesis scheme 8

8β-VINYL-11β-(ω-SUBSTITUTED)ALKYL-ESTRA-1,3,5(10)-TRIENES

This application claims the benefit of the filing date of U.S. Provisional Application Ser. No. 60/464,630 filed Apr. 23, 2003.

This invention relates to 8β-vinyl-11β-(ω-substituted) alkyl-estra-1,3,5(10)-trienes with ERβ-antagonistic activity, process for their production, their intermediate products, pharmaceutical preparations that contain the compounds according to the invention, as well as their use for the production of pharmaceutical agents.

The compounds according to the invention are those steroidal tissue-selective estrogens that have in vitro a higher affinity to estrogen receptor preparations from rat prostates than to estrogen receptor preparations from the rat uterus and that exert in vivo a contraceptive action by their preferential action on the ovary and are distinguished by an improved physicochemical profile.

Contraceptive methods with chemical compounds are common in women who do not want to become pregnant. The following chemical methods of female contraception are currently available:
1) Suppression of ovulation by inhibition of the gonadotropin release and thus the ovulation (the endocrine principle);
2) Prevention of the ascension of sperm through the female reproductive tract to the fallopian tube, where fertilization takes place;
3) Prevention of the implantation or nidation of a fertilized embryo in the uterus;
4) Spermicides;
5) Abortion-inducing agent.

Oral contraceptives that consist of the most varied combinations of an estrogen with a gestagen are the most frequently used contraceptives of women. They act according to the endocrine principle. Although such contraceptives are very effective, undesirable side effects can occur, such as, e.g.: irregular bleeding, nausea, vomiting, depression, weight gain or headaches. More serious diseases are also sometimes observed such as thromboembolisms, stroke, liver adenomas, gallbladder diseases or high blood pressure. These undesirable side effects of the oral contraceptives now used make clear the medical need for a new contraceptive method without side effects.

An ideal contraceptive method is a method that operates directly on the ovarian follicle without influencing the endocrine hypothalamus-pituitary gland-ovary axis. This could be achieved with a chemical compound that impairs the folliculogenesis, for example by destroying a paracrine interaction between the egg cells and the granulosa cells and thus sees to it that
a) the follicle program cannot adequately proceed such that an incompetent egg cell matures that specifically is ovulated but cannot be fertilized, or
b) the follicle program cannot adequately proceed, such that an incompetent egg cell matures, which specifically is ovulated and fertilized, but does not result in any pre-implantation development, or
c) the folliculogenesis is possible only to a limited extent, and no ovulation results.

Follicular growth is the development of an ovarian follicle from the primordial stage up to the large antral crack-free follicle. Only an optimally built-up antral follicle has the potential to ovulate a mature egg cell. Patients with ovarian infertility, e.g., PCOS (=policystic ovarian syndrome) patients, have a disrupted folliculogenesis associated with hormone and ovulation disorders as well as insufficiently matured egg cells (Franks et al., Mol. Cell. Endocrinol. 2000, 163, 49-52).

There are always more indications that the early stages of folliculogenesis, i.e., the development steps from primordial follicle up to early antral follicle, are gonadotropin-independent, but it is still not exhaustively clarified as to which of the identified autocrine or paracrine factors (Elvin et al., Mol. Cell. Endocrinol. 1999, 13, 1035-1048; McNatty et al., J. Reprod. Fertil. Suppl. 1999, 54, 3-16) are the most important in early folliculogeneis. Gonadotropins, such as, e.g., the follicle-stimulating hormone (FSH), however, are mainly involved in the late steps of folliculogenesis, i.e., the development of early antral to the large ovulatory follicle. Also, however, in late folliculogenesis, additional modulators of folliculogenesis are discussed (Elvin et al., Mol. Cell. Endocrinol. 1999, 13, 1035-1048).

Recently, the estrogen receptor-β (ERβ) was discovered as the second subtype of the estrogen receptor (Kuiper et al., Proc. Natl. Acad. Sci. 1996, 93, 5925-5930; Mosselman, Dijkema, FEBS Letters 1996, 392, 49-53; Tremblay et al., Molecular Endocrinology 1997, 11, 353-365). The expression pattern of ERβ differs from that of the ERα (Kuiper et al., Endocrinology 1996, 138, 863-870). While an expression of ERα could be detected in almost all organs studied, the highest expression of ERβ was found in female animals in the ovary and in male animals in the prostate (Couse et al., Endocrinology 1997, 138, 4613-4621). In the ovary, a significant ERβ expression in the follicles is shown in almost all development stages. While in the follicles, ERα is expressed only in the outer follicle cells (theca cells), a strong expression of ERβ is present in the estradiol-producing granulosa cells. Based on the different cell distribution of ERα and ERβ in the ovarian follicle, it can thus be expected that the interaction of a ligand with ERα or ERβ results in different cellular responses. The fact that ERα and ERβ are functionally different was recently confirmed by the successful production of ERα and ERβ knockout mice (Couse et al., Endocrine Reviews 1999, 20, 358-417). ERα is consequently involved in the function of the uterus, mammary glands, the control of the sexual-endocrine axis, while ERβ is mainly included in the processes of ovarian physiology, especially folliculogenesis and ovulation.

Another organ system with a higher ERβ expression is the testis (Mosselmann et al., FEBS Lett. 1996, 392, 49-53) including the spermatides (Shugrue et al., Steroids 1998, 63, 498-504). The fact that ERβ is functional in the male animal also follows by studies on ERα-(ERKO) or ERβ-(βERKO)-knockout mice: male ERKO mice (R. A. Hess et al., Nature 1997, 390, 509-512) exhibit significant fertility disorders. To this end, the important function of estrogens with respect to maintaining the testis function relative to fertility is confirmed.

ERα and ERβ have significantly different amino acid sequences in their ligand-binding and transactivating domains. This suggests that
(1) ER subtypes bind their ligands with different affinity, and
(2) Ligands of different agonistic and/or antagonistic potential can develop on the two receptor subtypes.

Patent Applications WO 00/47603, WO 00/63228, WO 01/32680, WO 01/77138, U.S. 60/207,370 as well as publications (Sun et al., Endocrinology 1999, 140, 800-804; Stauffer et al., J. Comb. Chem. 2000, 2, 318-329) show that steroidal and nonsteroidal ligands with high affinity to ERα and ERβ were found. Several compounds were considerably stronger agonists/antagonists at ERα, while other compounds were stronger agonists/antagonists at ERβ.

In WO 00/31112, new steroidal compounds based on the building block of the unsubstituted estradiol in 8-position, which carry a hydrocarbon radical in 11β-position, which contains an individual linear chain with a length of 5 to 9 carbon atoms, are described. These compounds have an ERα-agonistic/ERβ-antagonistic profile of action. Based on this mixed estrogen receptor profile, these compounds are suitable as improved estrogens for the treatment of estrogen-produced disorders and for contraception together with a gestagen.

In WO 02/068548, for the first time in vivo findings are shown from which it is clear that ERβ-selective agonists lead to an improvement in folliculogenesis, while ERβ-selective antagonists reduce the fertility, i.e., the ovulation rate.

WO 01/77138 discloses 11β-n-pentyl-und 11β-n-hexyl-8β-substituted estra-1,3,5(10)-trienes with ERβ-antagonistic action. The 11β-n-alkyl substitution, however, results in further reduction in polarity and thus also in poorer water-solubility of such compounds.

The object of this invention is to provide compounds with improved physicochemical properties that have in vitro a dissociation with respect to the binding to estrogen receptor preparations of rat prostates and rat uteri and exert a contraceptive action in vivo by their preferred action on the ovary, without influencing other estrogen-sensitive organs, such as, e.g., the uterus or the liver. These compounds are also to be used for male contraception as well as for treating benign or malignant proliferative diseases of the ovary.

This object is achieved according to the invention by the provision of the compounds of general formula I.

This invention relates to compounds of general formula I

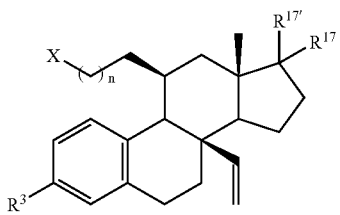

I in which
R$^3$ represents a group R$^{19}$—O—, R$^{20}$SO$_2$—O—, or —O—C(O)R$^{21}$;
n represents 3, 4, or 5:
x represents a group of formula II

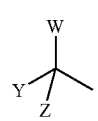

II in which
Z and W, independently of one another, represent R$^{19}$,
or
Z and W together represent an oxygen atom,
Y represents OR$^{19}$, —CN, —SCN, a halogen atom, R$^{20}$, R$^{20}$SO$_2$—O—;

or
Y represents R$^{19}$ or R$^{20}$, if Z and W together represent an oxygen atom;
R$^{17}$ and R$^{17'}$ together represent an oxygen atom, or a group =CR$^{23}$R$^{24}$, in which
R$^{23}$ and R$^{24}$, independently of one another, represent a hydrogen atom or a halogen;

or
R$^{17}$ represents hydrogen, —OR$^{19}$ or halogen;
R$^{17'}$ represents R$^{19}$, —OR$^{19}$, halogen, R$^{20}$SO$_2$—O—, —C(O)R$^{21}$ or —O—C(O)R$^{21}$;
R$^{19}$ represents a hydrogen atom,
a radical of formula C$_p$F$_q$H$_r$ with p=1, 2, 3, 4, 5, 6, 7, 8, 9; q>1 and q+r=2p+1;
an unbranched C$_1$-C$_8$-alkyl group or branched C$_3$-C$_6$-alkyl group, a C$_3$-C$_6$-cycloalkyl group that is optionally substituted with a phenyl radical, a (C$_3$-C$_6$-cycloalkyl)-C$_1$-C$_4$-alkylene group, a branched or unbranched C$_2$-C$_5$-alkenyl group, a C$_2$-C$_5$-alkinyl group; or an unsubstituted or substituted aryl-, heteroaryl-, heterocyclyl-, aryl-C$_1$-C$_4$-alkylene-, or heteroaryl-C$_1$-C$_4$-alkylene group;
R$^{20}$ represents an R$^{21}$R$^{22}$N— group, a group —C(NOR$^{19}$)H, or a group of general formula III

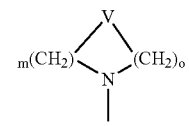

III in which
V represents —CH$_2$—, an oxygen atom or a sulfur atom, or =N—R$^{25}$;
m represents 0, 1, 2, 3, 4, 5, 6, 7 or 8;
o represents 0, 1, 2, 3, 4, 5, 6, 7 or 8, whereby their sum
m+o is 2, 3, 4, 5, 6, 7, 8, 9, 10, 11, 12;
R$^{21}$ and R$^{22}$, independently of one another, represent R$^{19}$;
R$^{25}$ represents R$^{19}$, R$^{20}$SO$_2$— or an acyl group —C(O)R$^{21}$.

This invention also comprises the pharmaceutically compatible salts of the compounds of general formula I according to the invention.

The unbranched C$_1$-C$_8$-alkyl group can be, for example, a methyl-, ethyl-, n-propyl-, n-butyl-, n-pentyl-, n-hexyl-, n-heptyl-, or n-octyl-; the branched C$_3$-C$_8$-alkyl group is an iso-propyl-, iso-butyl-, sec-butyl, tert-butyl-, iso-pentyl-, neo-pentyl-, 2-methylpentyl-, 2,2-dimethylbutyl-, 2,3-dimethylbutyl-, 2-methylhexyl-, 2,2-dimethylpentyl-, 2,2,3-trimethylbutyl-, or 2,3,3-trimethylbutyl group.

The C$_3$-C$_6$-cycloalkyl groups that are optionally substituted with a phenyl radical can readily be a cyclopropyl-, cyclobutyl-, cyclopentyl-, cyclohexyl-, or phenylcyclopropyl-, phenylcyclobutyl-, phenylcyclopentyl-, or phenylcyclohexyl group.

The (C$_3$-C$_6$-cycloalkyl)-C$_1$-C$_4$-alkylene group can be, for example, a cyclopropylmethyl-, cyclobutylmethyl-, cyclopentylmethyl-, cyclohexylmethyl, cyclopropylethyl-, cyclobutylethyl-, cyclopentylethyl-, cyclohexylethyl-, cyclopropylpropyl-, cyclobutylpropyl-, cyclopentylpropyl-, cyclohexylpropyl-, cyclopropylbutyl-, cyclobutylbutyl, cyclopentylbutyl- or cyclohexylbutyl group.

The branched or unbranched $C_2$-$C_5$-alkenyl group can be, for example, a vinyl-, trifluorovinyl-, allyl-, homoallyl-, (E)-but-2-enyl-, (Z)-but-2-enyl-, (E)-but-1-enyl-, (Z)-but-1-enyl-, pent-4-enyl-, (E)-pent-3-enyl-, (Z)-pent-3-enyl-, (E)-pent-2-enyl-, (Z)-pent-2-enyl-, (E)-pent-1-enyl-, (Z)-pent-1-enyl-, 2-methylvinyl-, 3-methylbut-3-enyl-, 2-methylbut-3-enyl-, (E)-2-methylbut-2-enyl-, (Z)-2-methylbut-2-enyl-, or 3-methylbut-2-enyl-group.

The $C_2$-$C_5$-alkinyl group can be, for example, an ethinyl-, prop-1-inyl-, prop-2-inyl-, but-1-inyl-, but-2-inyl-, but-3-inyl-, pent-1-inyl-, pent-2-inyl-, pent-3-inyl-, pent-4-inyl-, 1-methylprop-2-inyl-, 1-methylbut-3-inyl-, or 1-ethylprop-2-inyl group.

The $R^{19}O$ group accordingly can be, for example, a methoxy-, ethoxy-, n-propoxy-, iso-propoxy-, n-butoxy-, sec-butoxy-, iso-butoxy-, or tert-butoxy group.

An aryl group can be, for example, a phenyl-, naphthalen-1-yl-, naphthalen-2-yl-, [1,1'-biphenyl]-2-yl-, [1,1'-biphenyl]-3-yl group or a [1,1'-biphenyl]-4-yl group.

The heteroaryl group can be a pyridinyl-, pyrimidinyl-, quinolinyl-, isoquinolinyl-, benzofuranyl-, benzothienyl-, 1,3-benzodioxolyl-, 2,1,3-benzothiadiazolyl-, indolyl-, furanyl-, thienyl-, oxazolyl-, isoxazolyl-, thiazolyl-, pyrrolyl-, pyrazolyl-, pyrazinyl-, pyridazinyl group or an imidazolyl group that is linked by one of the points that can be substituted.

The heterocyclyl group for radicals Z and Z' can be a piperidinyl-, morpho-linyl-, thiomorpholinyl-, piperazinyl-, tetrahydrofuranyl-, tetrahydrothienyl-, imidazolidinyl group or a pyrrolidinyl group that can be linked by one of the points that can be substituted.

The substituent of the aryl, heteroaryl and heterocyclyl radicals can be, i.a., unbranched or branched $C_1$-$C_4$-alkyl groups (methyl-, ethyl-, n-propyl-, iso-propyl-, n-butyl-, sec-butyl-, iso-butyl- as well as tert-butyl-) and/or $C_2$-$C_6$-alkenyl groups (vinyl-, allyl-, homoallyl-, (E)-but-2-enyl-, (Z)-but-2-enyl-, pent-4-enyl-, (E)-pent-3-enyl-, (Z)-pent-3-enyl-, (E)-pent-2-enyl-, (Z)-pent-2-enyl-, 2-methylvinyl-, 3-methylbut-3-enyl-, 2-methylbut-3-enyl-, (E)-2-methylbut-2-enyl-, (Z)-2-methylbut-2-enyl-, 2-ethylprop-2-enyl-, hex-5-enyl-, (E)-hex-4-enyl-, (Z)-hex-4-enyl-, (E)-hex-3-enyl-, (Z)-hex-3-enyl-, (E)-hex-2-enyl-, (Z)-hex-2-enyl-, 1-methylpent-4-enyl-, (E)-1-methylpent-3-enyl-, (Z)-1-methylpent-3-enyl-, 1-ethylbut-3-enyl-, (E)-1-methylpent-2-enyl-, (Z)-1-methylpent-2-enyl-) and/or $C_3$-$C_6$-cycloalkyl groups (cyclopropyl-, cyclobutyl-, cyclopentyl-, cyclohexyl-), and/or halogen (fluorine, chlorine, bromine, or iodine), and/or —OH, —O—($C_1$-$C_4$-alkyl), formyl-, —$CO_2$H, —$CO_2$($C_1$-$C_4$-alkyl), —$NO_2$, —$N_3$, —CN, $C_1$-$C_8$-acyl-, $C_1$-$C_8$-acyloxy-, trifluoromethyl-, pentafluoroethyl-, methylthio-, trifluoromethylthio-, and/or amino-, mono($C_1$-$C_8$-alkyl)amino- or di($C_1$-$C_8$-alkyl)amino, whereby both alkyl groups are identical or different.

The aryl-$C_1$-$C_4$-alkylene group for radicals Z and Z' can be a combination of the above-defined aryl and $C_1$-$C_4$-alkyl groups, for example: a phenylmethyl-, 1-phenylethyl-, 2-phenylethyl-, 1-methyl-1-phenylethyl-, 3-phenylpropyl-4-phenylbutyl-, (naphthalen-1-yl)methyl-, 1-(Naphthalen-1-yl)ethyl-, 2-(naphthalen-1-yl)-ethyl-, (naphthalen-2-yl)methyl-, 1-(naphthalen-2-yl)ethyl-, 2-(naphthalen-2-yl)ethyl-, ([1,1'-biphenyl]-2-yl)methyl-, ([1,1'-biphenyl]-3-yl)methyl- or a ([1,1'-biphenyl]-4-yl)methyl group.

The heteroaryl-$C_1$-$C_4$-alkylene groups for radicals Z and Z' can be a combination of the above-defined heteroaryl- and $C_1$-$C_4$-alkylene groups, for example a (pyridin-2-yl)methyl-, (pyridin-3-yl)methyl-, (pyridin-4-yl)methyl-, (furan-2-yl)methyl-, (furan-3-yl)methyl-, (thien-2-yl)methyl-, (thien-3-yl)methyl-, 2-(thien-2-yl)ethyl- or a 2-(thien-3-yl)ethyl group.

The radical of formula $C_pF_qH_r$ with p=1, 2, 3, 4, 5, 6, 7, 8, 9; q>1 and q+r=2p+1 can be a monofluoromethyl-, difluoromethyl-, trifluoromethyl-, pentafluoroethyl-, perfluoropropyl-, perfluorobutyl-, 2,2,2-trifluoroethyl-, 5,5,5,4,4-pentafluoropentyl-, 6,6,6,5,5,4,4,3,3-nonafluorohexyl-, 9,9,9,8,8-pentafluorononyl-, or 9,9,9,8,8,7,7-heptafluorononyl group.

According to the invention, halogen is fluorine, chlorine, bromine or iodine.

For the formation of pharmaceutically compatible salts of the compounds of general formula I according to the invention, the following are considered according to the methods that are known to one skilled in the art: as inorganic acids, i.a., hydrochloric acid, hydrobromic acid, sulfuric acid and phosphoric acid, nitric acid; as carboxylic acids, i.a., acetic acid, propionic acid, hexanoic acid, octanoic acid, decanoic acid, oleic acid, stearic acid, maleic acid, fumaric acid, succinic acid, benzoic acid, ascorbic acid, oxalic acid, salicylic acid, tartaric acid, citric acid, lactic acid, glycolic acid, malic acid, mandelic acid, cinnamic acid, glutaminic acid, asparaginic acid; as sulfonic acids, i.a., methanesulfonic acid, ethanesulfonic acid, toluenesulfonic acid, benzenesulfonic acid as well as naphthalenesulfonic acid.

Preferred according to this invention are those compounds of general formula I, in which Y means —OH, —CN, —SCN, a halogen atom, or $R^{20}$;

or

Y means $R^{20}$, if Z and W together represent an oxygen atom.

Especially preferred according to this invention are those compounds of general formula I, in which Y represents —OH, —CN, —SCN, a halogen atom, or $R^{20}$;

or

Y represents $R^{20}$, if Z and W together represent an oxygen atom, and $R^{17}$ and $R^{17'}$ together represent an oxygen atom, or $R^{17}$ represents hydrogen, or —OH;

$R^{17'}$ represents hydrogen, —OH, $C_1$-$C_4$-alkyl group, $C_2$-$C_5$-alkenyl group, a $C_2$-$C_5$-alkinyl group, or a trifluoromethyl group.

The compounds according to the invention that are mentioned below are quite especially preferred. In the case of epimeric alcohols, the two possible diastereomers are also quite especially preferred.

11β-[(R)6,6,6-Trifluoro-5-hydroxyhexyl]-8-vinyl-estra-1,3,5(10)-triene-3,17β-diol (Diastereomer 1), 11β-[(S)6,6,6-Trifluoro-5-hydroxyhexyl]-8-vinyl-estra-1,3,5(10)-triene-3,17β-diol (Diastereomer 2), 11β-[7,7,7-Trifluoro-6-hydroxyheptyl]-8-vinyl-estra-1,3,5(10)-triene-3,17β-diol (Diastereomer 1), 11β-[7,7,7-Trifluoro-6-hydroxyheptyl]-8-vinyl-estra-1,3,5(10)-triene-3,17β-diol (Diastereomer 2), 11β-[8,8,8-Trifluoro-7-hydroxyoctyl]-8-vinyl-estra-1,3,5 (10)-triene-3,17β-diol, (Diastereomer 1),
11β-[8,8,8-Trifluoro-7-hydroxyoctyl]-8-vinyl-estra-1,3,5 (10)-triene-3,17β-diol (Diastereomer 2),
11β-[6,6,6-Trifluoro-5-hydroxy-5-(trifluoromethyl)hexyl]-8-vinyl-estra-1,3,5(10)-triene-3,17β-diol,
11β-[7,7,7-Trifluoro-6-hydroxy-6-(trifluoromethyl)heptyl]-8-vinyl-estra-1,3,5(10)-triene-3,17β-diol,
11β-[8,8,8-Trifluoro-7-hydroxy-7-(trifluoromethyl)octyl]-8-vinyl-estra-1,3,5(10)-triene-3,17β-diol,
11β-[7,7,7,6,6-Pentafluoro-5-hydroxyheptyl]-8-vinyl-estra-1,3,5(10)-triene-3,17β-diol (Diastereomer 1),
11β-[7,7,7,6,6-Pentafluoro-5-hydroxyheptyl]-8-vinyl-estra-1,3,5(10)-triene-3,17β-diol (Diastereomer 2),
11β-[8,8,8,7,7-Pentafluoro-6-hydroxyoctyl]-8-vinyl-estra-1,3,5(10)-triene-3,17β-diol (Diastereomer 1),
11β-[8,8,8,7,7-Pentafluoro-6-hydroxyoctyl]-8-vinyl-estra-1,3,5(10)-triene-3,17β-diol (Diastereomer 2),
11β-[9,9,9,8,8-Pentafluoro-7-hydroxynonyl]-8-vinyl-estra-1,3,5(10)-triene-3,17β-diol (Diastereomer 1),
11β-[9,9,9,8,8-Pentafluoro-7-hydroxynonyl]-8-vinyl-estra-1,3,5(10)-triene-3,17β-diol (Diastereomer 2),
11β-[8,8,8,7,7,6,6-Heptafluoro-5-hydroxyoctyl]-8-vinyl-estra-1,3,5(10)-triene-3,17β-diol (Diastereomer 1),
11β-[8,8,8,7,7,6,6-Heptafluoro-5-hydroxyoctyl]-8-vinyl-estra-1,3,5(10)-triene-3,17β-diol (Diastereomer 2),
11β-[9,9,9,8,8,7,7-Heptafluoro-6-hydroxynonyl]-8-vinyl-estra-1,3,5(10)-triene-3,17β-diol (Diastereomer 1),
11β-[9,9,9,8,8,7,7-Heptafluoro-6-hydroxynonyl]-8-vinyl-estra-1,3,5(10)-triene-3,17β-diol (Diastereomer 2),
11β-[10,10,10,9,9,8,8-Heptafluoro-7-hydroxydecyl]-8-vinyl-estra-1,3,5(10)-triene-3,17β-diol (Diastereomer 1),
11β-[10,10,10,9,9,8,8-Heptafluoro-7-hydroxydecyl]-8-vinyl-estra-1,3,5(10)-triene-3,17β-diol (Diastereomer 2),
11β-(5-Bromopentyl)-8-vinyl-estra-1,3,5(10)-triene-3,17β-diol,
11β-[5-(Methylamino)pentyl]-8-vinylestra-1,3,5(10)-triene-3,17β-diol,
11β-[5-(Dimethylamino)pentyl]-8-vinylestra-1,3,5(10)-triene-3,17β-diol,
11β-[5-(Pyrrolidin-1-yl)pentyl]-8-vinylestra-1,3,5(10)-triene-3,17β-diol,
11β-[5-(1-Piperidyl)pentyl]-8-vinylestra-1,3,5(10)-triene-3,17β-diol,
11β-(5-Morpholinopentyl)-8-vinylestra-1,3,5(10)-triene-3,17β-diol,
11β-{5-[Methyl(9,9,9,8,8-pentafluorononyl)amino]pentyl}-8-vinylestra-1,3,5(10)-triene-3,17β-diol,
11β-{5-[(9,9,9,8,8,7,7-Heptafluorononyl)methylamino]pentyl}-8-vinylestra-1,3,5(10)-triene-3,17β-diol,
11β-{5-[Methyl(octanoyl)amino]pentyl}-8-vinyl-estra-1,3,5(10)-triene-3,17β-diol,
11β-(6-Chlorohexyl)-8-vinyl-estra-1,3,5(10)-triene-3,17β-diol,
11β-[6-(Methylamino)hexyl]-8-vinylestra-1,3,5(10)-triene-3,17β-diol,
11β-[6-(Dimethylamino)hexyl]-8-vinylestra-1,3,5(10)-triene-3,17β-diol,
11β-[6-(Pyrrolidin-1-yl)hexyl]-8-vinylestra-1,3,5(10)-triene-3,17β-diol,
11β-[6-(1-Piperidyl)hexyl]-8-vinylestra-1,3,5(10)-triene-3,17β-diol,
11β-(6-Morpholinohexyl)-8-vinylestra-1,3,5(10)-triene-3,17β-diol,
11β-{6-[Methyl(9,9,9,8,8-pentafluorononyl)amino]hexyl}-8-vinylestra-1,3,5(10)-triene-3,17β-diol,
11β-{6-[(9,9,9,8,8,7,7-Heptafluorononyl)methylamino]hexyl}-8-vinylestra-1,3,5(10)-triene-3,17β-diol,
11β-{6-[Methyl(octanoyl)amino]hexyl}-8-vinyl-estra-1,3,5(10)-triene-3,17β-diol,
11β-(7-Bromoheptyl)-8-vinyl-estra-1,3,5(10)-triene-3,17β-diol,
11β-[7-(Methylamino)heptyl]-8-vinylestra-1,3,5(10)-triene-3,17β-diol,
11β-[7-(Dimethylamino)heptyl]-8-vinylestra-1,3,5(10)-triene-3,17β-diol,
11β-[7-(Pyrrolidin-1-yl)heptyl]-8-vinylestra-1,3,5(10)-triene-3,17β-diol,
11β-[7-(1-Piperidyl)heptyl]-8-vinylestra-1,3,5(10)-triene-3,17β-diol,
11β-(7-Morpholinoheptyl)-8-vinylestra-1,3,5(10)-triene-3,17β-diol,
11β-{7-[Methyl(9,9,9,8,8-pentafluorononyl)amino]heptyl}-8-vinylestra-1,3,5(10)-triene-3,17β-diol,
11β-{7-[(9,9,9,8,8,7,7-Heptafluorononyl)methylamino]heptyl}-8-vinylestra-1,3,5(10)-triene-3,17β-diol,
11β-{7-[Methyl(octanoyl)amino]heptyl}-8-vinyl-estra-1,3,5(10)-triene-3,17β-diol,
N-nButyl-N-methyl-5-[3,17β-dihydroxy-8-vinylestra-1,3,5(10)-trien-11β-yl]valeramide,
N-nButyl-N-methyl-6-[3,17β-dihydroxy-8-vinylestra-1,3,5(10)-trien-11β-yl]capronamide,
N-nButyl-N-methyl-7-[3,17β-dihydroxy-8-vinylestra-1,3,5(10)-trien-11β-yl]enanthoamide,
11β-(5-Thiocyanatopentyl)-8-vinylestra-1,3,5(10)-triene-3,17β-diol,
11β-(6-Thiocyanatohexyl)-8-vinylestra-1,3,5(10)-triene-3,17β-diol,
11β-(7-Thiocyanatoheptyl)-8-vinylestra-1,3,5(10)-triene-3,17β-diol,
6-[3,17β-Dihydroxy-8-vinylestra-1,3,5(10)-trien-11β-yl]capronitrile,
7-[3,17β-Dihydroxy-8-vinylestra-1,3,5(10)-trien-11β-yl]enanthonitrile,
17β-Hydroxy-11β-[(R)6,6,6-trifluoro-5-hydroxyhexyl]-8-vinyl-estra-1,3,5(10)-trien-3-yl-sulfamate (Diastereomer 1),
17β-Hydroxy-11β-[(S)6,6,6-trifluoro-5-hydroxyhexyl]-8-vinyl-estra-1,3,5(10)-trien-3-yl-sulfamate (Diastereomer 2),
17β-Hydroxy-11β-[7,7,7-trifluoro-6-hydroxyheptyl]-8-vinyl-estra-1,3,5(10)-trien-3-yl-sulfamate (Diastereomer 1),
17β-Hydroxy-11β-[7,7,7-trifluoro-6-hydroxyheptyl]-8-vinyl-estra-1,3,5(10)-trien-3-yl-sulfamate (Diastereomer 2),
17β-Hydroxy-11β-[8,8,8-trifluoro-7-hydroxyoctyl]-8-vinyl-estra-1,3,5(10)-trien-3-yl-sulfamate, (Diastereomer 1),
17β-Hydroxy-11β-[8,8,8-trifluoro-7-hydroxyoctyl]-8-vinyl-estra-1,3,5(10)-trien-3-yl-sulfamate (Diastereomer 2),
17β-Hydroxy-11β-[6,6,6-trifluoro-5-hydroxy-5-(trifluoromethyl)hexyl]-8-vinyl-estra-1,3,5(10)-trien-3-yl-sulfamate,
17β-Hydroxy-11β-[7,7,7-trifluoro-6-hydroxy-6-(trifluoromethyl)heptyl]-8-vinyl-estra-1,3,5(10)-trien-3-yl-sulfamate,
17β-Hydroxy-11β-[8,8,8-trifluoro-7-hydroxy-7-(trifluoromethyl)octyl]-8-vinyl-estra-1,3,5(10)-trien-3-yl-sulfamate,
17β-Hydroxy-11β-[7,7,7,6,6-pentafluoro-5-hydroxyheptyl]-8-vinyl-estra-1,3,5(10)-trien-3-yl-sulfamate (Diastereomer 1), 17β-Hydroxy-11β-[7,7,7,6,6-pentafluoro-5-hydroxyheptyl]-8-vinyl-estra-1,3,5(10)-trien-3-yl-sulfamate (Diastereomer 2),
17β-Hydroxy-11β-[8,8,8,7,7-pentafluoro-6-hydroxyoctyl]-8-vinyl-estra-1,3,5(10)-trien-3-yl-sulfamate (Diastereomer 1),
17β-Hydroxy-11β-[8,8,8,7,7-pentafluoro-6-hydroxyoctyl]-8-vinyl-estra-1,3,5(10)-trien-3-yl-sulfamate (Diastereomer 2),
17β-Hydroxy-11β-[9,9,9,8,8-pentafluoro-7-hydroxynonyl]-8-vinyl-estra-1,3,5(10)-trien-3-yl-sulfamate (Diastereomer 1),
17β-Hydroxy-11β-[9,9,9,8,8-pentafluoro-7-hydroxynonyl]-8-vinyl-estra-1,3,5(10)-trien-3-yl-sulfamate (Diastereomer 2),
11β-[5-(Dimethylamino)pentyl]-17β-hydroxy-8-vinylestra-1,3,5(10)-trien-3-yl-sulfamate,
17β-Hydroxy-11β-[5-(pyrrolidin-1-yl)pentyl]-8-vinylestra-1,3,5(10)-trien-3-yl-sulfamate,
17β-Hydroxy-11β-[5-(1-piperidyl)pentyl]-8-vinylestra-1,3,5(10)-trien-3-yl-sulfamate,
17β-Hydroxy-11β-(5-morpholinopentyl)-8-vinylestra-1,3,5(10)-trien-3-yl-sulfamate,
11β-[6-(Dimethylamino)hexyl]-17β-hydroxy-8-vinylestra-1,3,5(10)-trien-3-yl-sulfamate,
17β-Hydroxy-11β-[6-(pyrrolidin-1-yl)hexyl]-8-vinylestra-1,3,5(10)-trien-3-yl-sulfamate,
17β-Hydroxy-11β-[6-(1-piperidyl)hexyl]-8-vinylestra-1,3,5(10)-trien-3-yl-sulfamate,
17β-Hydroxy-11β-(6-morpholinohexyl)-8-vinylestra-1,3,5(10)-trien-3-yl-sulfamate,
11β-[7-(dimethylamino)heptyl]-17β-hydroxy-8-vinylestra-1,3,5(10)-trien-3-yl-sulfamate,
17β-Hydroxy-11β-[7-(pyrrolidin-1-yl)heptyl]-8-vinylestra-1,3,5(10)-trien-3-yl-sulfamate,
17β-Hydroxy-11β-[7-(1-piperidyl)heptyl]-8-vinylestra-1,3,5(10)-trien-3-yl-sulfamate,
17β-Hydroxy-11β-(7-morpholinoheptyl)-8-vinylestra-1,3,5(10)-trien-3-yl-sulfamate,
11β-[7,7,6-Trifluoro-5-hydroxyhept-6-enyl]-8-vinyl-estra-1,3,5(10)-triene-3,17β-diol (Diastereomer 1),
11β-[7,7,6-Trifluoro-5-hydroxyhept-6-enyl]-8-vinyl-estra-1,3,5(10)-triene-3,17β-diol (Diastereomer 2),
11β-[8,8,7-Trifluoro-6-hydroxyoct-7-enyl]-8-vinyl-estra-1,3,5(10)-triene-3,17β-diol (Diastereomer 1),
11β-[8,8,7-Trifluoro-6-hydroxyoct-7-enyl]-8-vinyl-estra-1,3,5(10)-triene-3,17β-diol (Diastereomer 2),
11β-[9,9,8-Trifluoro-7-hydroxynon-8-enyl]-8-vinyl-estra-1,3,5(10)-triene-3,17β-diol (Diastereomer 1),
11β-[9,9,8-Trifluoro-7-hydroxynon-8-enyl]-8-vinyl-estra-1,3,5(10)-triene-3,17β-diol (Diastereomer 2),
11β-[5-Hydroxyhexyl]-8-vinyl-estra-1,3,5(10)-triene-3,17β-diol (Diastereomer 1),
11β-[5-Hydroxyhexyl]-8-vinyl-estra-1,3,5(10)-triene-3,17β-diol (Diastereomer 2),
11β-[6-Hydroxyheptyl]-8-vinyl-estra-1,3,5(10)-triene-3,17β-diol (Diastereomer 1),
11β-[6-Hydroxyheptyl]-8-vinyl-estra-1,3,5(10)-triene-3,17β-diol (Diastereomer 2),
11β-[7-Hydroxyoctyl]-8-vinyl-estra-1,3,5(10)-triene-3,17β-diol (Diastereomer 1),
11β-[7-Hydroxyoctyl]-8-vinyl-estra-1,3,5(10)-triene-3,17β-diol (Diastereomer 2),
11β-[5-Methyl-5-hydroxyhexyl]-8-vinyl-estra-1,3,5(10)-triene-3,17β-diol,
11β-[6-Methyl-6-hydroxyheptyl]-8-vinyl-estra-1,3,5(10)-triene-3,17β-diol,
11β-[7-Methyl-7-hydroxyoctyl]-8-vinyl-estra-1,3,5(10)-triene-3,17β-diol,
17α-Methyl-11β-[(R)6,6,6-trifluoro-5-hydroxyhexyl]-8-vinyl-estra-1,3,5(10)-triene-3,17β-diol (Diastereomer 1),
17α-Methyl-11β-[(S)6,6,6-trifluoro-5-hydroxyhexyl]-8-vinyl-estra-1,3,5(10)-triene-3,17β-diol (Diastereomer 2),
17α-Methyl-11β-[7,7,7-trifluoro-6-hydroxyheptyl]-8-vinyl-estra-1,3,5(10)-triene-3,17β-diol (Diastereomer 1),
17α-Methyl-11β-[7,7,7-trifluoro-6-hydroxyheptyl]-8-vinyl-estra-1,3,5(10)-triene-3,17β-diol (Diastereomer 2),
17α-Methyl-11β-[8,8,8-trifluoro-7-hydroxyoctyl]-8-vinyl-estra-1,3,5(10)-triene-3,17β-diol (Diastereomer 1),
17α-Methyl-11β-[8,8,8-trifluoro-7-hydroxyoctyl]-8-vinyl-estra-1,3,5 (10)-triene-3,17β-diol (Diastereomer 2),
17β-Hydroxy-11β-[8,8,8,7,7,6,6-heptafluoro-5-hydroxyoctyl]-8-vinyl-estra-1,3,5(10)-trien-3-yl-sulfamate (Diastereomer 1),
17β-Hydroxy-11β-[8,8,8,7,7,6,6-heptafluoro-5-hydroxyoctyl]-8-vinyl-estra-1,3,5(10)-trien-3-yl-sulfamate (Diastereomer 2),
17β-Hydroxy-11β-[9,9,9,8,8,7,7-heptafluoro-6-hydroxynonyl]-8-vinyl-estra-1,3,5(10)-trien-3-yl-sulfamate (Diastereomer 1),
17β-Hydroxy-11β-[9,9,9,8,8,7,7-heptafluoro-6-hydroxynonyl]-8-vinyl-estra-1,3,5(10)-trien-3-yl-sulfamate (Diastereomer 2),
17β-Hydroxy-11β-[10,10,10,9,9,8,8-heptafluoro-7-hydroxydecyl]-8-vinyl-estra-1,3,5(10)-trien-3-yl-sulfamate (Diastereomer 1),
17β-Hydroxy-11β-[10,10,10,9,9,8,8-heptafluoro-7-hydroxydecyl]-8-vinyl-estra-1,3,5(10)-trien-3-yl-sulfamate (Diastereomer 2),
17β-Hydroxy-11β-[7,7,6-trifluoro-5-hydroxyhept-6-enyl]-8-vinyl-estra-1,3,5(10)-trien-3-yl-sulfamate (Diastereomer 1),
17β-Hydroxy-11β-[7,7,6-trifluoro-5-hydroxyhept-6-enyl]-8-vinyl-estra-1,3,5(10)-trien-3-yl-sulfamate (Diastereomer 2),
17β-Hydroxy-11β-[8,8,7-trifluoro-6-hydroxyoct-7-enyl]-8-vinyl-estra-1,3,5(10)-trien-3-yl-sulfamate (Diastereomer 1),
17β-Hydroxy-11β-[8,8,7-trifluoro-6-hydroxyoct-7-enyl]-8-vinyl-estra-1,3,5(10)-trien-3-yl-sulfamate (Diastereomer 2),
17β-Hydroxy-11β-[9,9,8-trifluoro-7-hydroxynon-8-enyl]-8-vinyl-estra-1,3,5(10)-trien-3-yl-sulfamate (Diastereomer 1),
17β-Hydroxy-11β-[9,9,8-trifluoro-7-hydroxynon-8-enyl]-8-vinyl-estra-1,3,5(10)-trien-3-yl-sulfamate (Diastereomer 2),
17β-Hydroxy-17α-methyl-11β-[(R)6,6,6-trifluoro-5-hydroxyhexyl]-8-vinyl-estra-1,3,5(10)-trien-3-yl-sulfamate (Diastereomer 1),
17β-Hydroxy-17α-methyl-11β-[(S)6,6,6-trifluoro-5-hydroxyhexyl]-8-vinyl-estra-1,3,5(10)-trien-3-yl-sulfamate (Diastereomer 2),
17β-Hydroxy-17α-methyl-11β-[7,7,7-trifluoro-6-hydroxyheptyl]-8-vinyl-estra-1,3,5(10)-trien-3-yl-sulfamate (Diastereomer 1),
17β-Hydroxy-17α-methyl-11β-[7,7,7-trifluoro-6-hydroxyheptyl]-8-vinyl-estra-1,3,5(10)-trien-3-yl-sulfamate (Diastereomer 2),
17β-Hydroxy-17α-methyl-11β-[8,8,8-trifluoro-7-hydroxyoctyl]-8-vinyl-estra-1,3,5(10)-trien-3-yl-sulfamate (Diastereomer 1), 17β-Hydroxy-17α-methyl-11β-[8,8,8-trifluoro-7-hydroxy-octyl]-8-vinyl-estra-1,3,5(10)-trien-3-yl-sulfamate (Diastereomer 2).

The compounds according to the invention are suitable for inhibiting folliculogenesis and ovulation, for male contraception and for treating benign and malignant proliferative diseases of the ovary.

Unlike the estrogen ethinylestradiol that is usually used for hormonal contraception or else the compounds to be used for contraception according to WO 00/31112, the compounds of general formula I according to the invention can be used alone for contraception, i.e., without the additional administration of gestagens.

The ester derivatives of the estratrienes according to the invention can have advantages as prodrugs compared to the unesterified active ingredients with respect to their method of administration, their type of action, strength of action and duration of action.

The sulfamate derivatives of the estratrienes according to the invention also have pharmacokinetic and pharmacodynamic advantages. Such effects were already described in other steroid-sulfamates (J. Steroid Biochem. Molec. Biol. 1995, 55, 395-403; Exp. Opinion Invest. Drugs 1998, 7, 575-589).

This invention describes 8β-vinyl-11β-(ω-substituted) alkyl-estra-1,3,5(10)-trienes, which have in vitro dissociation with respect to binding to estrogen receptor preparations of rat prostates and rat uteri and which have in vivo preferably an inhibition of folliculogenesis and ovulation. The compounds according to the invention have a contraceptive action over a broad dose range, without influencing other estrogen-sensitive organs, such as, e.g., the uterus or the liver.

Moreover, these compounds can be used for male contraception and for treating benign or malignant proliferative diseases of the ovary.

This invention therefore relates to pharmaceutical preparations that contain at least one compound of general formula I as well as their physiologically compatible salts, the use of the compounds of general formula I for the production of a pharmaceutical agent for male and/or female contraception, and for the treatment of benign and malignant proliferative diseases of the ovary.

The compounds according to the invention can be used for the following indications both after oral and parenteral administration.

The compounds of general formula I according to the invention can be used as individual components in pharmaceutical preparations or in combination especially with GnRH antagonists, progesterone receptor antagonists, mesoprogestins, gestagens or tissue-selective gestagens (action on A/B-form type).

The compounds according to the invention and the preparations that contain them are especially suitable for ovarian contraception, for the treatment of benign or malignant proliferative diseases of the ovary, such as, e.g., ovarian cancer, and granulosa cell tumors.

In addition, the compounds can be used for treating male fertility disorders and prostatic diseases.

The amount of a compound of general formula I that is to be administered varies within a wide range and can cover any effective amount. On the basis of the condition that is to be treated and the type of administration, the amount of the compound that is administered can be 0.01 μg/kg-100 mg/kg of body weight, preferably 0.04 μg/kg-1 mg/kg of body weight, per day.

In humans, this corresponds to a dose of 0.8 μg to 8 g, preferably 3.2 μg to 80 mg, daily.

According to the invention, a dosage unit contains 1.6 μg to 2000 mg of one or more compounds of general formula I.

The compounds according to the invention and their acid addition salts are suitable for the production of pharmaceutical compositions and preparations. The pharmaceutical compositions or pharmaceutical agents contain as active ingredients one or more of the compounds according to the invention or their acid addition salts, optionally mixed with other pharmacologically or pharmaceutically active substances. The production of the pharmaceutical agents is carried out in a known way, whereby the known and commonly used pharmaceutical adjuvants as well as other commonly used vehicles and diluents can be used.

As such vehicles and adjuvants, for example, those are suitable that are recommended or indicated in the following bibliographic references as adjuvants for pharmaceutics, cosmetics and related fields: Ullmans Encyklopädie der technischen Chemie [Ullman's Encyclopedia of Technical Chemistry], Volume 4 (1953), pages 1 to 39; Journal of Pharmaceutical Sciences, Volume 52 (1963), page 918 ff., issued by Czetsch-Lindenwald, Hilfsstoffe für Pharmazie und angrenzende Gebiete [Adjuvants for Pharmaceutics and Related Fields]; Pharm. Ind., Issue 2, 1961, p. 72 and ff.: Dr. H. P. Fiedler, Lexikon der Hilfsstoffe für Pharmazie, Kosmetik und angrenzende Gebiete [Dictionary of Adjuvants for Pharmaceutics, Cosmetics and Related Fields], Cantor K G, Aulendorf in Württemberg 1971.

The compounds according to the invention can be administered orally or parenterally, for example intraperitoneally, intramuscularly, subcutaneously or percutaneously, or else implanted in the tissue.

For oral administration, capsules, pills, tablets, coated tablets, etc., are suitable. In addition to the active ingredient, the dosage units can contain a pharmaceutically compatible vehicle, such as, for example, starch, sugar, sorbitol, gelatin, lubricant, silicic acid, talc, etc.

For parenteral administration, the active ingredients can be dissolved or suspended in a physiologically compatible diluent. As diluents, very often oils with or without the addition of a solubilizer, a surfactant, a suspending agent or an emulsifying agent are used. Examples of oils that are used are olive oil, peanut oil, cottonseed oil, soybean oil, castor oil and sesame oil.

The compounds can also be used in the form of a depot injection or an implant preparation, which can be formulated so that a delayed release of active ingredient is made possible.

As inert materials, implants can contain, for example, biodegradable polymers, or synthetic silicones such as, for example, silicone rubber. In addition, for percutaneous administration, the active ingredients can be added to, for example, a patch.

For the production of intravaginal systems (e.g., vaginal rings) or intrauterine systems (e.g., pessaries, coils, IUDs) that are loaded with active compounds of general formula I for local administration, various polymers are suitable, such as, for example, silicone polymers, ethylene vinyl acetate, polyethylene or polypropylene.

To achieve better bio-availability of the active ingredient, the compounds can also be formulated as cyclodextrin clathrates. For this purpose, the compounds are reacted with α-, β-, or γ-cyclodextrin or derivatives of the latter (PCT/EP95/02656).

The compounds of general formula I according to the invention can also be encapsulated with liposomes.

BRIEF DESCRIPTION OF THE DRAWINGS

FIG. 1 depicts a general operating scheme for synthesis of Aldehyde 9a

PHARMACOLOGICAL STUDIES

Estrogen Receptor Binding Studies

Figure 1:
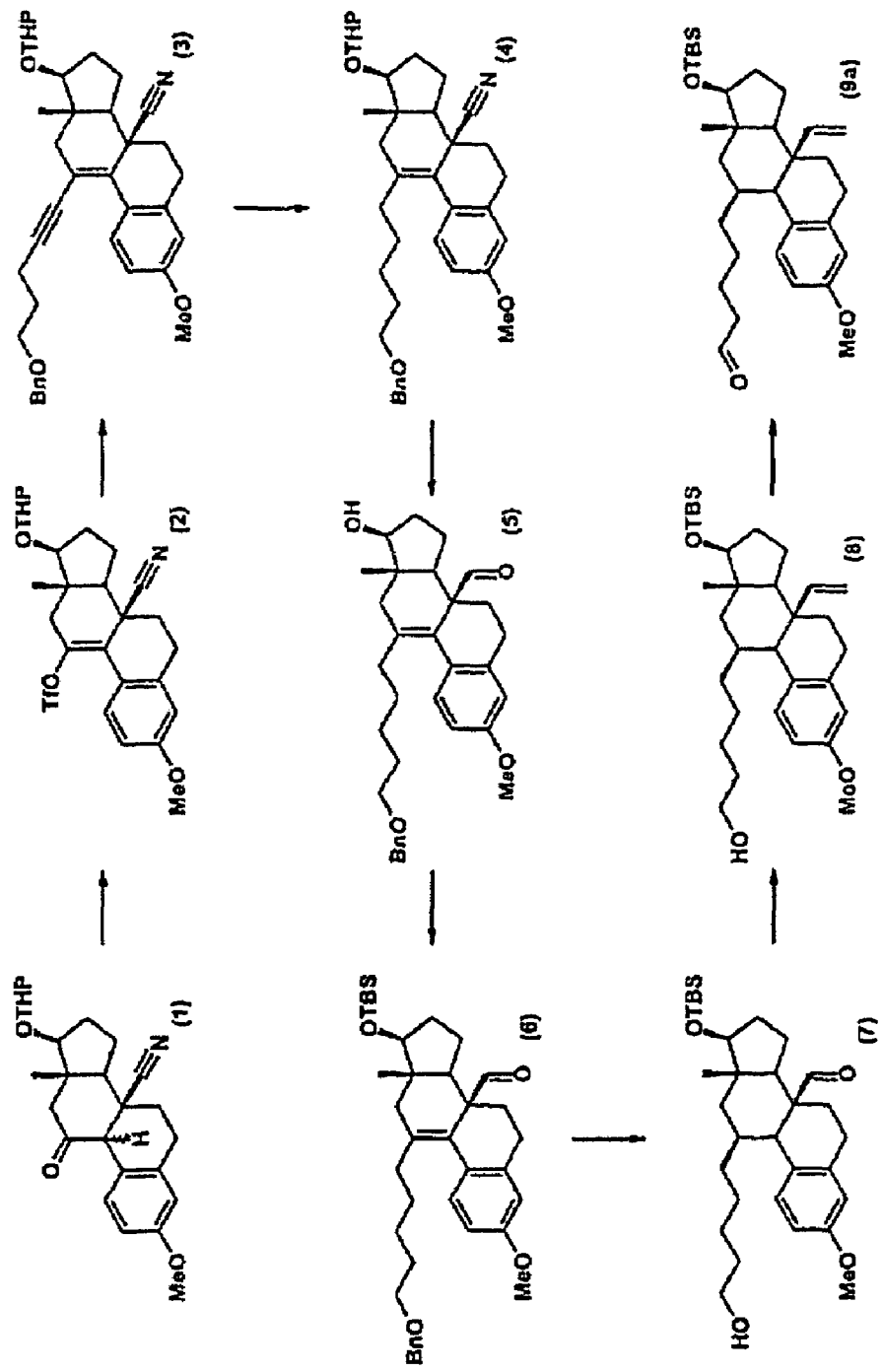
Figure 2:
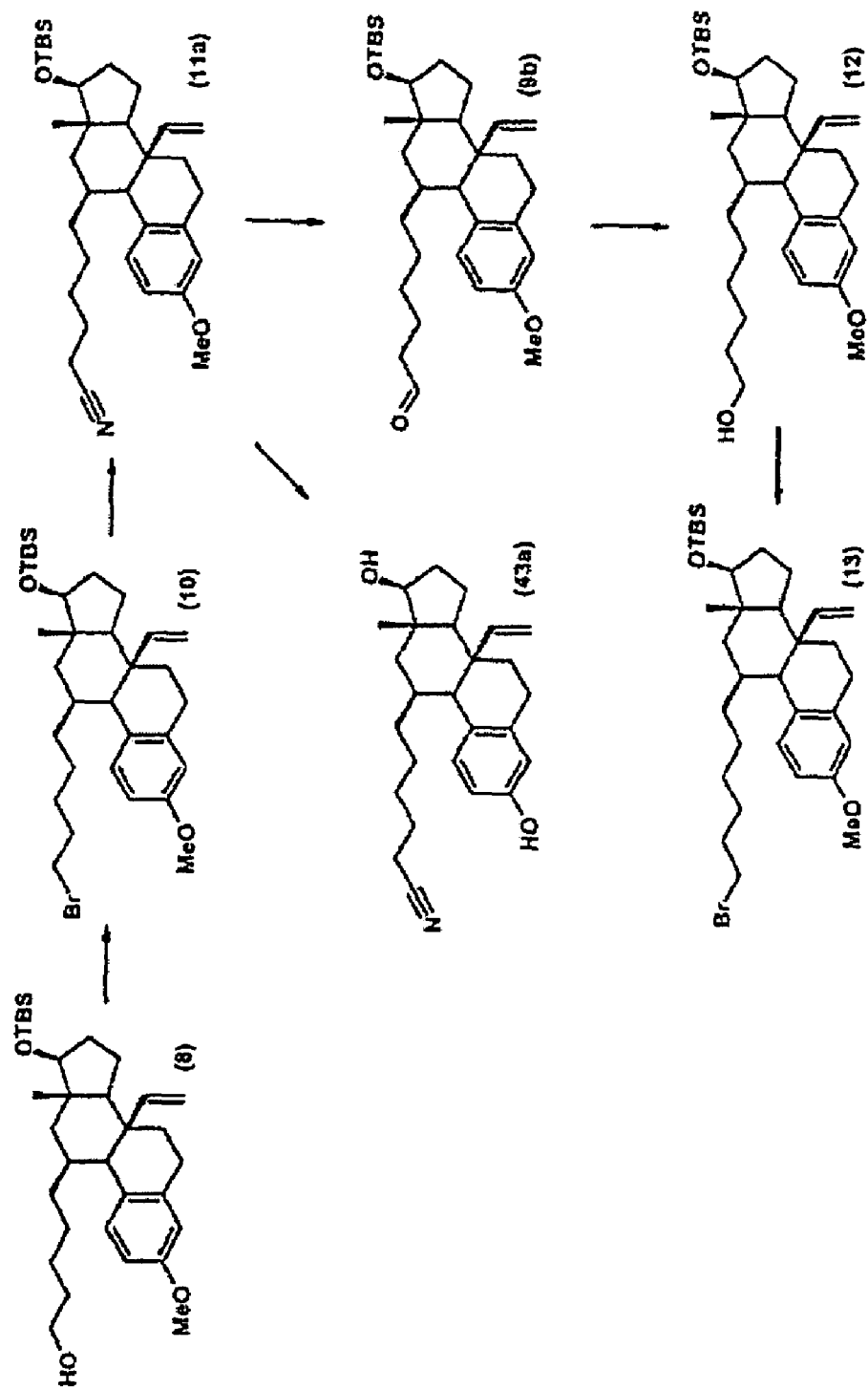
FIG. 2 depicts a general operating scheme for synthesis of Aldehyde 9b
Figure 3:
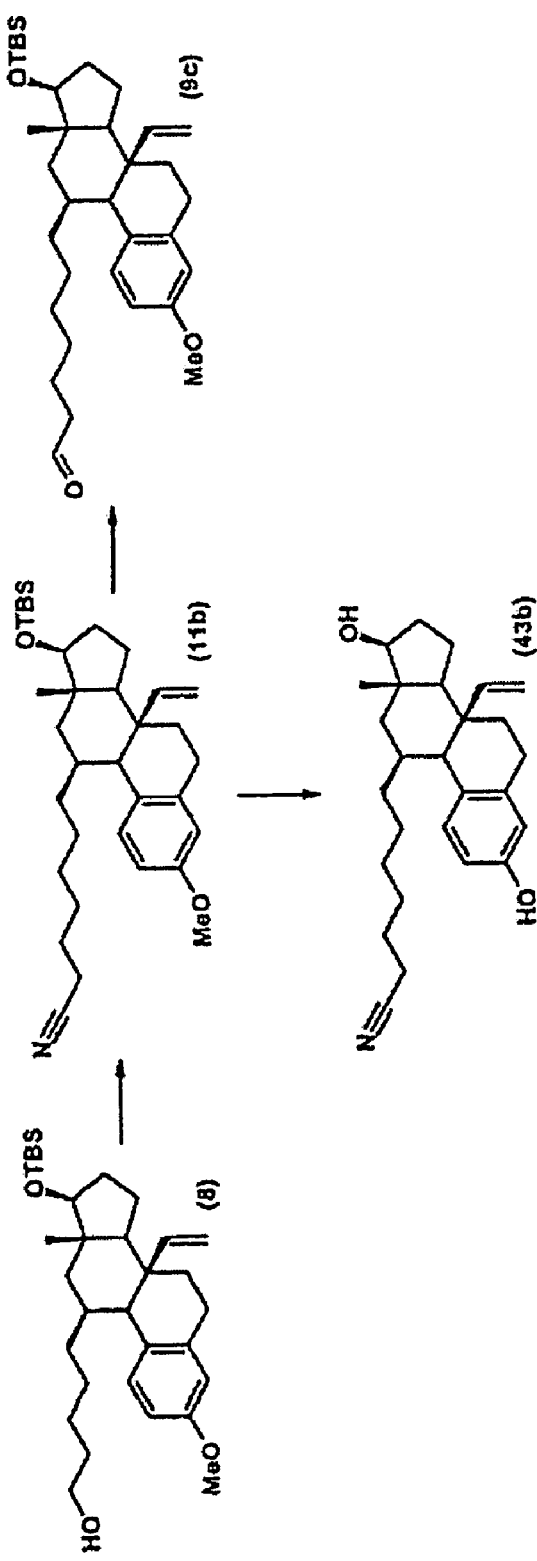
FIG. 3 depicts a general operating scheme for synthesis of Aldehyde 9c
Figure 4:
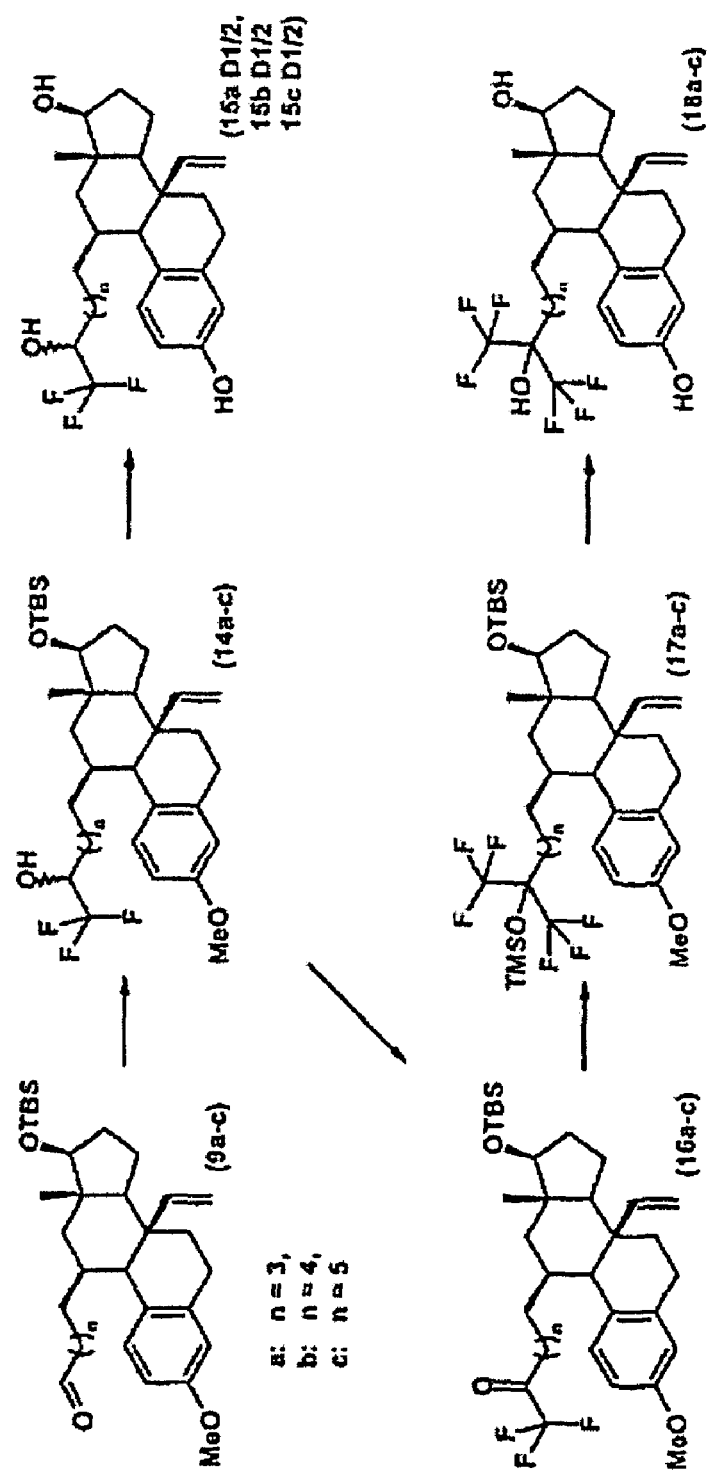
FIG. 4 depicts a General Operating scheme
Figure 5:
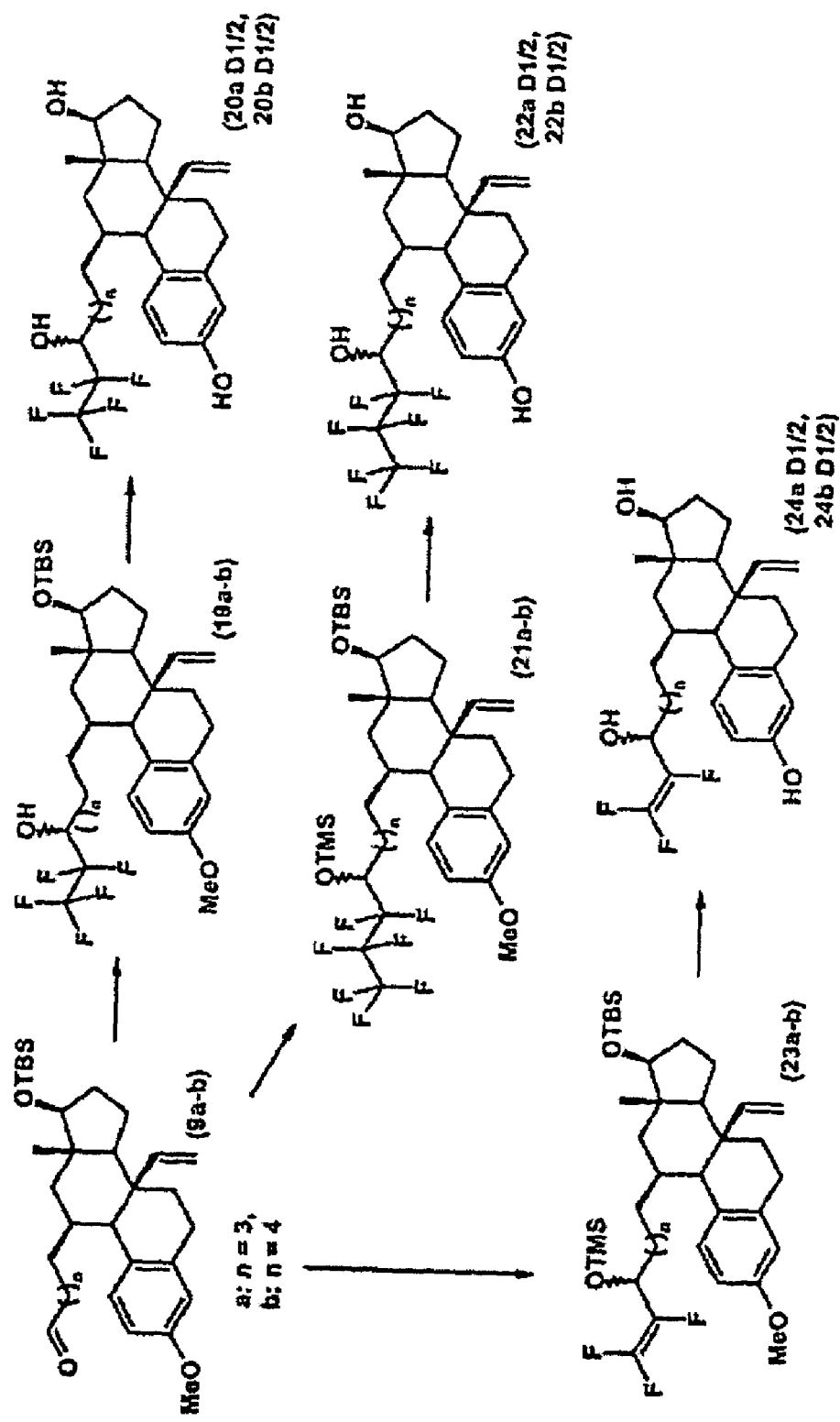
FIG. 5 depicts a General Operating scheme
Figure 6:
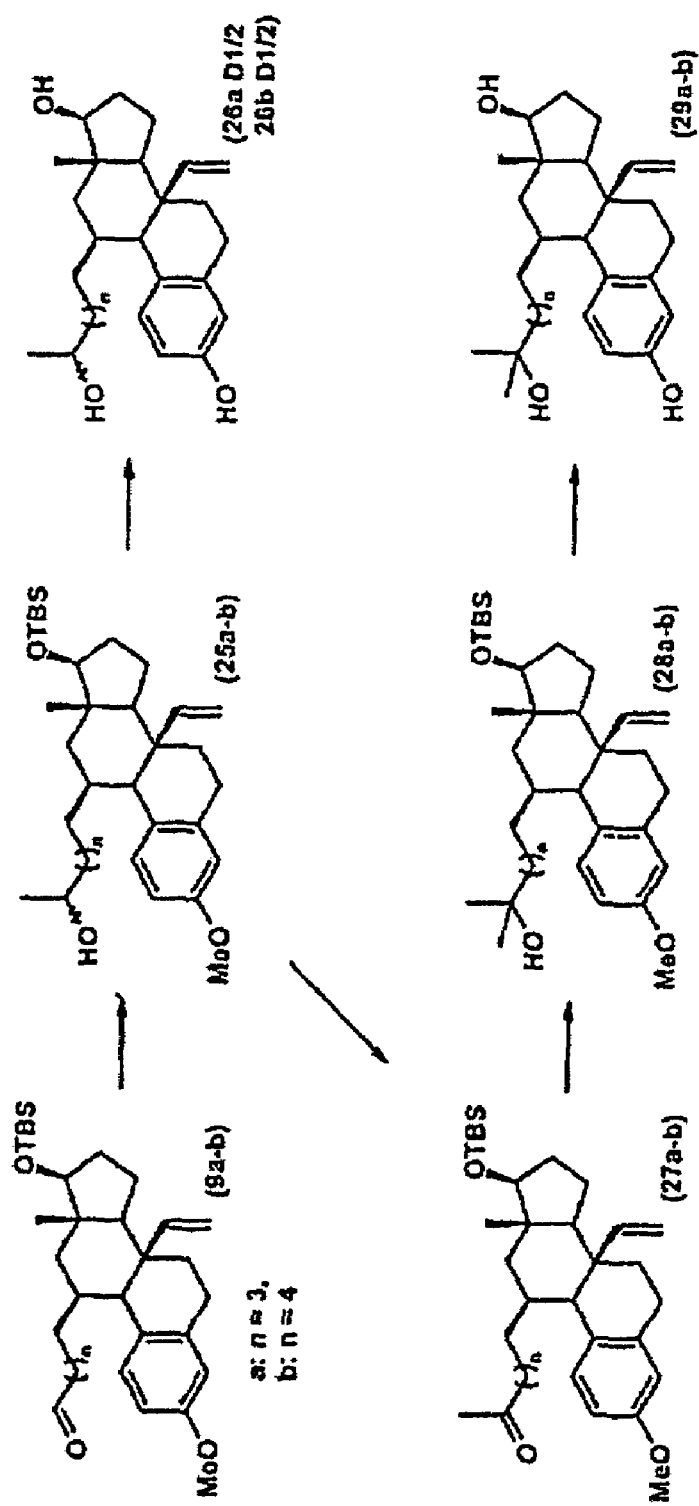
FIG. 6 depicts a general operating scheme
Figure 7:
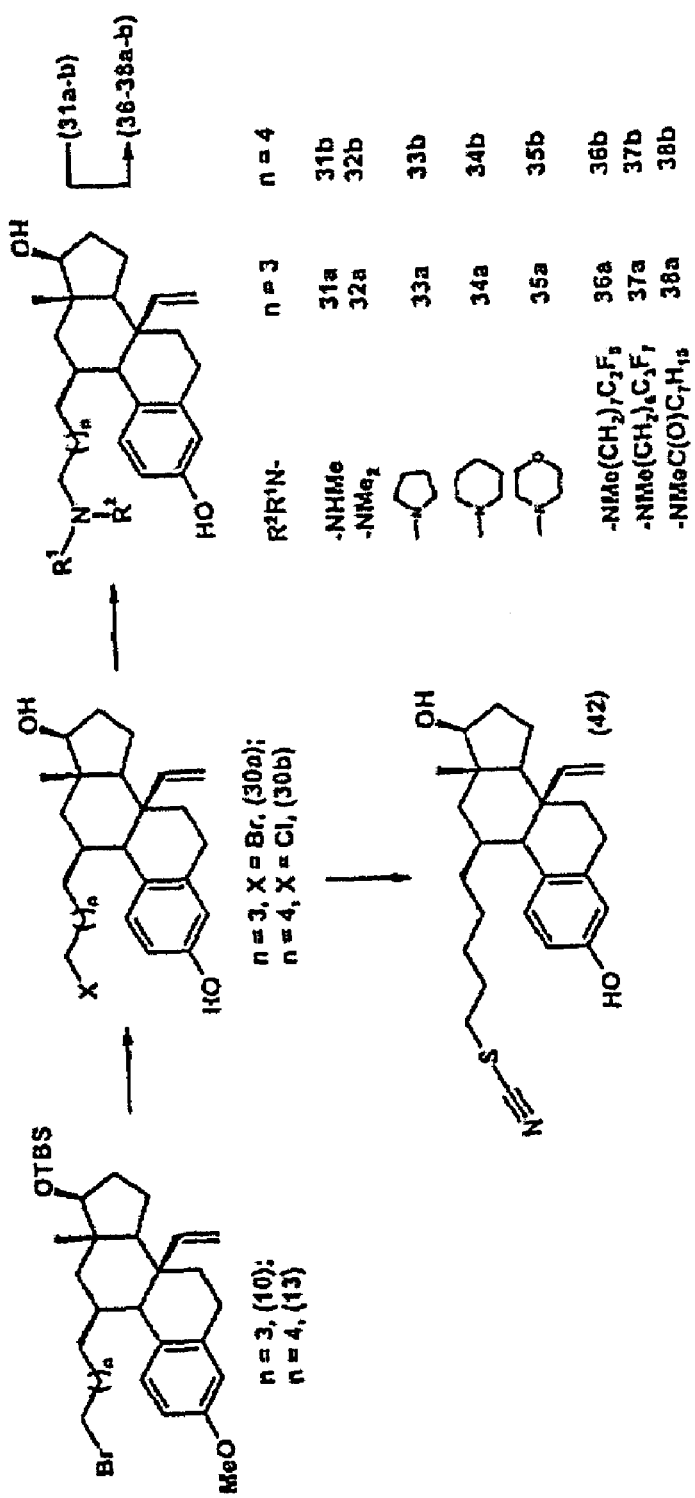
FIG. 7 depicts a general operating scheme for the introduction of an amino Group and for acylation of amines
Figure 8:
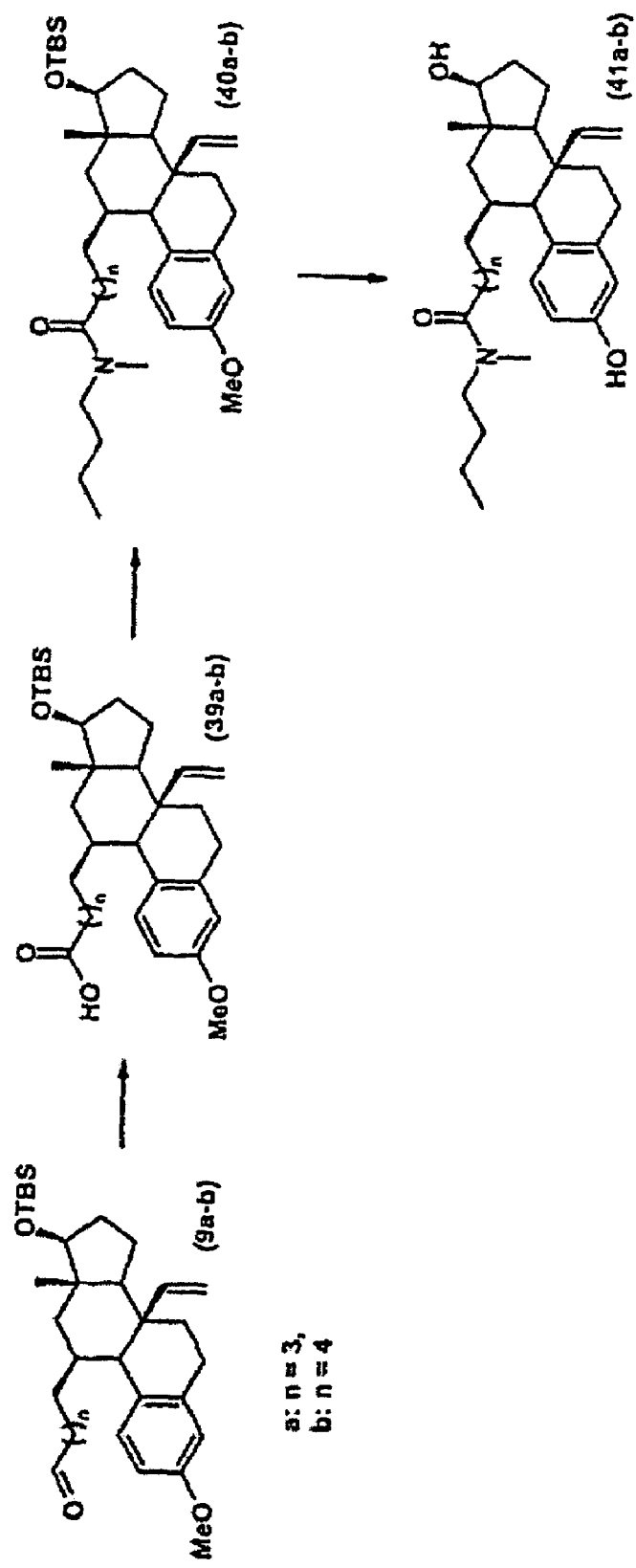
FIG. 8 depicts a general operating scheme for the oxidation of Aldehydes.

The binding affinity of the compounds according to the invention was tested in competitive experiments with use of 3H-estradiol as a ligand on estrogen receptor preparations from rat prostates and rat uteri. The preparation of prostate cytosol and the estrogen receptor test with prostate cytosol was carried out as described by J. Testas et al. in Endocrinology 1981, 109, 1287-1289.

The preparation of rat uterus cytosol as well as the receptor test with the ER-containing cytosol were basically performed as described by Stack and Gorski in Endocrinology, 1985, 117, 2024-2032, with some modifications according to U. Fuhrmann et al. in Contraception, 1995, 51, 45-52.

The compounds according to the invention have higher binding affinity to the estrogen receptor from rat prostates than to estrogen receptors from rat uteri (Tables 1 and 2). In this case, it is assumed that ERβ predominates in the rat prostates over ERα, and ERα predominates in rat uteri over ERβ. Table 1 shows that the ratio of the binding to prostate and uterus receptors qualitatively coincides with the quotient of relative binding affinity (RBA) to human ERβ and ERα of rats (according to Kuiper et al. Endocrinology 1996, 138, 863-870) (Table 1).

TABLE 1

| Estrogen | hERα RBA | HERβ RBA | ERβ/ERα | Rat Uterus ER (RBA) | Rat Prostate ER (RBA) | Prost. ER/Uterus ER |
|---|---|---|---|---|---|---|
| 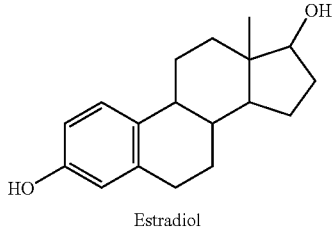 Estradiol | 100 | 100 | 1 | 100 | 100 | 1 |
| 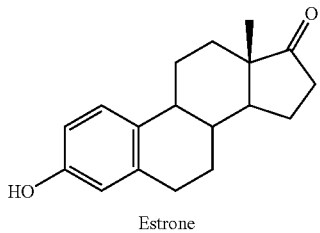 Estrone | 60 | 37 | 0.6 | 3 | 2 | 0.8 |
| 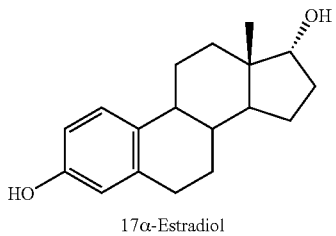 17α-Estradiol | 58 | 11 | 0.2 | 2.4 | 1.3 | 0.5 |

TABLE 1-continued

| Estrogen | hERα RBA | HER β RBA | ERβ/ ERα | Rat Uterus ER (RBA) | Rat Prostate ER (RBA) | Prost. ER/ Uterus ER |
|---|---|---|---|---|---|---|
| Estriol | 14 | 21 | 1.5 | 4 | 20 | 5 |
| 5-Androstenediol | 6 | 17 | 3 | 0.1 | 5 | 50 |
| Genisteine | 5 | 36 | 7 | 0.1 | 10 | 100 |
| Coumestrol | 94 | 185 | 2 | 1.3 | 24 | 18 |

*: cited from: Kuiper et al., Endocrinology 1996, 138, 863-870

Transactivation Test for Estrogenic Agonists and Antagonists

Cultivation of Cells:

U-2OS cells are cultivated in Dulbecco's medium (DMEM) without phenol red (Gibco BRL; #11880-028)+ 5% fetal calf serum (FCS) (Seromed; #S 0115) ⊥100 units/ml of penicillin/100 µg/ml of streptomycin (Seromed; #A 2213), 4 mmol of L-glutamine (Gibco BRL; #25030-024) (PSG) at 37° C. and 8.5% $CO_2$.

Cells that were held for at least 24 hours in D-MEM with 5% activated carbon-treated FCS(CCS)+PSG are washed and trypsinized with PBS-Dulbecco's (Gibco BRL; #14190-094) (trypsin/EDTA (0.05/0.02%); Seromed; #L 2153). The resuspension of the cells is carried out in 10 ml of D-MEM+ 5% CCS+PSG.

Dilution of $8 \times 10^6$ cells to 80 ml with D-MEM+5% CCS+PSG for eight 96-well plates (Packard; CulturePlate-96, #6005180). Dissemination of 100 µl of cell suspension ($1 \times 10^4$ cells) per well. 6 hours after the dissemination, the transfection takes place.

Transfection by Means of FuGENE 6:

The ERβα-expression plasmid (HEGO) that was used was amplified in E. coli DH5α (Invitrogen Company). The ERβ-expression plasmid (ERβ0) that was used was produced in-house and amplified in E. coli DH5α. As in the case of the ERα, the expression plasmid pSG5 was used. As a reporter plasmid, the vector pBL-LUC+ was provided with two Tandem-EREs (estrogen-responsive elements of the vitellogenin promoter) and amplified in E. coli (XL1-Blue; Stratagene Company).

Plasmid-DNA is prepared by means of the NucleoBond Plasmid Maxi Kit (CLONTECH; #K3003-2) and FuGENE 6 reagent (Boehringer Mannheim; #1 814 443). The latter are first diluted separately in a suitable volume of DMEM and incubated, before the solutions are combined and again incubated.

Batches for 96-Well Plates:

| DNA Mixture (A) | in the 50 ml-BlueMax (Falcon; #2070) tube |
|---|---|
| pSG5-ERα/β FL (Heg0/ERβ0) | 2 ng/well (Estrogen receptor-expression plasmid) |
| p(ERE)$_2$-luc$^+$ | 100 ng/well (Luciferase-reporter plasmid) |
| Transfection Reagent (B): | in a 14 ml-polypropylene tube (Falcon; #2059) |
| DMEM or Serum (introduction) | 9.7 µl/well |
| FuGENE 6 (directly into the medium) | 0.3 µl/well |

Incubation of solutions A and B for 5 minutes at room temperature (RT). Then solution B to be added drop by drop to solution A and mixed. Incubation of solution AB for 15 minutes at room temperature.

Dilution of the transfection mixture AB for 4 plates with 22.5 ml of D-MEM+5% CCS+PSG. 100 µl of this compound is added to the cells per well and incubated overnight (16-18 hours) at 8.5% $CO_2$ and 37° C. Only 60 wells are transfixed per plate; the outside wells receive only medium.

Hormone Treatment:

For dose-action curves, dilution series for reference and test substances are produced in 96-well plates (Costar; #3595), starting from $10^{-3}$M stock solutions dissolved in dimethyl sulfoxide (DMSO, Sigma; #D-2650). The $10^{-3}$M DMSO solutions are stored at −20° C. and must be readily dissolved before the removal (15 minutes, 37° C.).

The dilution stages are selected such that the final concentrations on the test plate for agonism lie in the range of $10^{-7}$-$10^{-12}$M (for $E_2$: $10^{-8}$-$10^{-13}$M).

All dilution stages thus contain 1% DMSO.

After the transfection, the transfection medium is replaced by 180 µl of D-MEM+5% CCS+PSG per well.

To test for antagonism, the cells are treated in addition with estradiol. Then, 20 µl of the substance dilutions is pipetted through. The negative controls receive 20 µl of DMEM+1% DMSO per well. The final test substance concentrations are $3 \times 10^{-11}$ M for ERα or $3 \times 10^{-10}$ M for ERβ. As a reference substance, the known antiestrogen fulvestrant (AstraZeneca) is used at the same concentration (Table 2).

The incubation is carried out overnight (16-18 hours) at 8.5% $CO_2$ and 37° C.

Lysis of the Cells and Determination of the Luciferase Activity:

After the medium is suctioned off, in each case 30 µl of lysis 1× reagent (Promega; #E1531) is added to the cells and incubated for ½ hour-1 hour at room temperature while being shaken vigorously (IKA-VIBRAX-VXR, 600 rpm).

Then, the lysates are mixed with 30 µl of luciferase substrate A (PharMingen; #556867) and 30 µl of luciferase substrate B (PharMingen; #556869). The measurement of the luciferase activity is carried out 30 seconds after substrate B is added in the cycle mode of the luminometer (DYNATECH; ML3000).

The evaluation of the measurement data is carried out by means of software assigned by the equipment manufacturer (BioLinx). The production of the results as dose-action curves for agonism and antagonism is carried out in the Sigma Plot program with mean values (n=3) and standard deviation. A calculation of $EC_{50}$, the efficacy and the EMR value for the agonism or the $IC_{50}$ and the efficacy for the antagonism is possible by means of "MTS" software (Table 2).

Physicochemical Profile:

In comparison to compounds from WO 01/77138, an improvement of the physiochemical profile according to the invention, with respect to the distribution coefficients [log D (HPLC method, pH: 7.0, 25° C.)] and/or the solubility [Sw (turbidimetry, pH 7.4 at 25° C.)], of the compounds according to the invention is achieved (Table 2).

Surprisingly enough, moreover, it was also possible to increase the potency at ERβ (EMR value) and/or the selectivity in favor of the ERβ.

TABLE 2

| Compound | # | MW | EMR ($EC_{50}$)[%] | | Efficacy[%] | | Log D | Sw [mg/l] |
|---|---|---|---|---|---|---|---|---|
| | | | ERα | ERβ | ERα | ERβ | | |
| (structure 1) | Ref.[1] | 606.78 | 100 (0.38 nmol) | 100 (0.49 nmol) | 100 | 100 | 5.31 | <1 |
| (structure 2) | Ref.[2] | 370.57 | 0.3 | 3.1 | 80 | 98 | — | — |

TABLE 2-continued

| Compound | # | MW | EMR (EC$_{50}$)[%] | | Efficacy[%] | | Log D | Sw [mg/l] |
|---|---|---|---|---|---|---|---|---|
| | | | ERα | ERβ | ERα | ERβ | | |
| (structure) | Ref.[2] | 382.58 | 0.5 | 18 | 63 | 93 | 5.7 | <1 |
| (structure) | 36 | 393.57 | 1.6 | 33 | 67 | 100 | — | — |
| (structure) | 35 | 425.63 | 0.7 | 33 | 93 | 95 | — | — |
| (structure) | 26b | 451.69 | 12 | 52 | 66 | 93 | 4.2 | 37 |
| (structure) | 26a | 437.66 | 7.9 | 56 | 85 | 100 | 4.0 | >40 |
| (structure) | 25b | 425.66 | 17 | 137 | 88 | 99 | 4.2 | >40 |
| (structure) | 24b | 411.63 | 8 | 60 | 85 | 99 | 4.0 | >40 |

TABLE 2-continued

| Compound | # | MW | EMR (EC$_{50}$)[%] ERα | EMR (EC$_{50}$)[%] ERβ | Efficacy[%] ERα | Efficacy[%] ERβ | Log D | Sw [mg/l] |
|---|---|---|---|---|---|---|---|---|
| | 22b D1/2 | 566.59 | 1.6 | 29 | 90 | 100 | 5.1 | 7 |
| | 18b | 534.58 | 1.6 | 19 | 85 | 100 | 4.7 | 3 |
| | 15b D1/2 | 466.58 | 5.0 | 80 | 76 | 100 | 4.1 | 5 |
| | 15a D1/2 | 452.55 | 0.8 | 42 | 79 | 100 | — | — |
| | 15a D2 | 452.55 | 0.8 | 50 | 86 | 100 | 3.6 | 11 |
| | 45a D2 | 466.58 | 1.2 | 50 | 68 | 100 | 4.1 | 11 |

[1] Comparison compound: fulvestrant
[2] WO 01/77138

Sample Studies of Contraceptive Action

Study of Early Folliculogenesis.

Immature female rats are treated from day 1 to day 4 with a combination of cetrorelix and the ERβ-selective estrogen 8β-vinylestra-1,3,5(10)-triene-3,17β-diol (25 mg/kg, s.c.). In addition, the vehicle or the active substance is administered in various dosages (1; 3; 10; 30 mg/kg, s.c.) from day 1 to day 4. The autopsy of the animals is carried out on day 5. The ovary is removed and analyzed macroscopically, e.g., organ weights, and microscopically, e.g., histological evaluation of the follicles, so-called follicle staging.

Study of Late Folliculogenesis/Ovulation

Immature female rats are hypophysectomized. This day is defined as day 0. From day 1-day 4, subcutaneous and/or oral treatment is carried out with the active substance in combination with 17β-estradiol. On day 5, a subcutaneous injection with PMSG (pregnant mare serum gonadotropin) is carried out. On day 7, hCG is administered intraperitoneally to trigger ovulation. On day 8, the ovary is removed and analyzed macroscopically (e.g., ovary weight) and/or microscopically (e.g., histological evaluation of the follicles, so-called follicle staging). The tubes are flushed and checked for the presence of egg cells.

Study of Ovulation

At the age of 23 days, immature female rats are treated subcutaneously with PMSG (pregnant mare serum gonadotropin) (day 1). On the same day, as well as 24 and 48 hours later, the animals receive the active substance, administered subcutaneously or orally. 54 hours after the PMSG injection, the animals receive an intraperitoneal injection of hCG to trigger ovulation. Autopsy is carried out 16 hours after the hCG is administered. The tubes are flushed and checked for the presence of eggs cells.

Another possibility to detect in vivo the dissociated estrogen action of the substances according to the invention consists in the fact that after a one-time administration of the substances in rats, effects on the expression of 5HT2a-receptor and serotonin transporter protein and mRNA levels in ERβ-rich brain areas can be measured. Compared to the effect on the serotonin receptor and transporter expression, the effect on the LH-secretion is measured. Substances with higher binding to the rat prostate—compared to the rat uterus estrogen receptor—are more potent with respect to increasing the expression of serotonin receptors and transporters, in comparison to their positive effect on the LH release. The density of serotonin receptors and transporters is determined in brain sections using radioactive ligands, and the corresponding mRNA is determined using in situ hybridization. The method is described in the literature: G. Fink & B. E. H. Sumner 1996 Nature 383: 306; B. E. H. Sumner et al. 1999 Molecular Brain Research, in press.

Production Processes for the Compounds According to the Invention

This invention also relates to the intermediate products of general formula VI

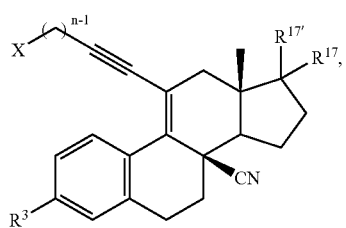

intermediate products of general formula VII

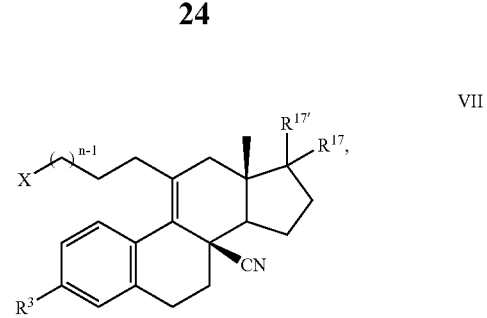

intermediate products of general formula VIII

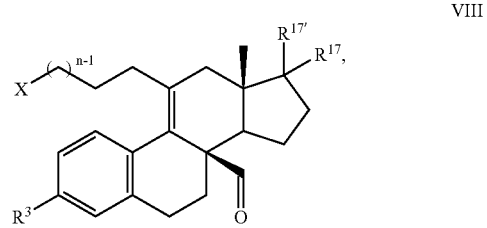

as well as intermediate products of general formula IX

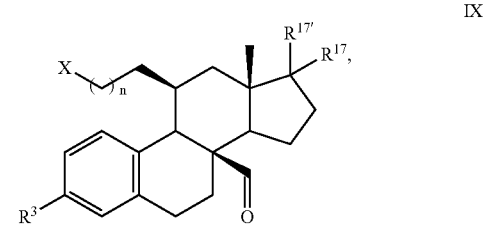

in which radicals X, $R^3$, $R^{17}$, $R^{17'}$ and n have the same meaning as in general formula I.

Compounds of general formulas IV to X are used as intermediate products in the production process to form compounds of general formula I:

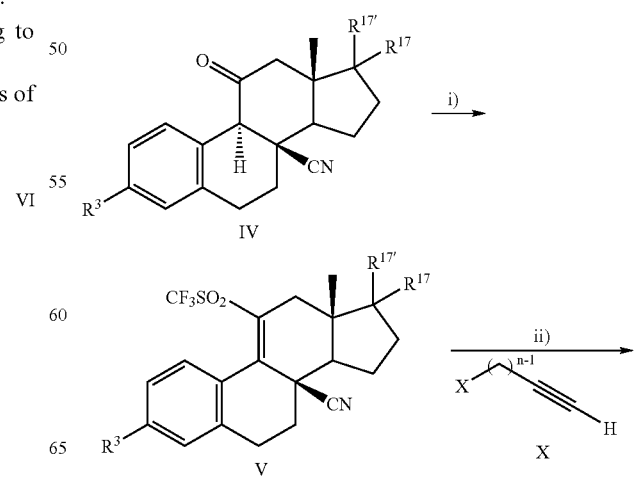

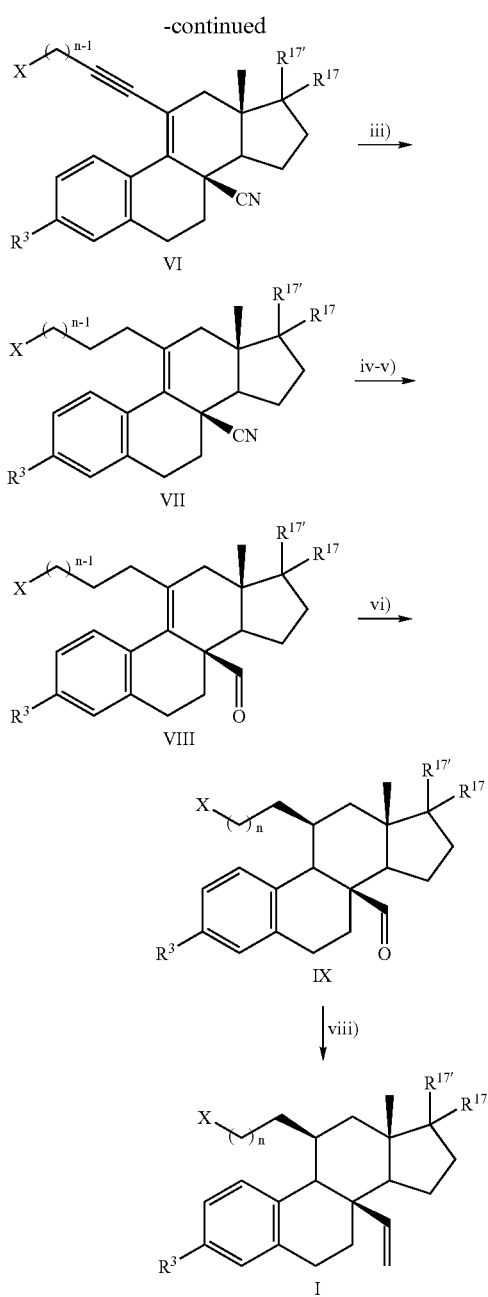

i) Trifluoromethanesulfonic acid anhydride/pyridine ii) Compound of general formula X, palladium(II)-acetate/triphenylphosphine/copper(I)-iodide/piperidine/50° C.

iii) Palladium/magnesium carbonate (10%)/1 bar of hydrogen/tetrahydrofuran/methanol iv) Diisobutyl aluminum hydride/toluene/0° C.

v) Protective group manipulation vi) a) Protective group manipulation,
b) Pd/C (10%)/100 bar of hydrogen/tetrahydrofuran/methanol vii) Wittig olefination with $Ph_3P=CH$ Compounds of general formula IV are accessible to one skilled in the art according to WO 01/77139; the intermediate stage of general formula V is also known from PCT/EP/02/11533.

In addition, this invention also relates to a process for the production of the compounds of general formula I, as well as, in each case, processes for the production of individual intermediate stages VI to IX.

The compounds of general formula I according to the invention can be produced as described in the Examples. By an analogous procedure using reagents homologous to the reagents that are described in the examples, the additional compounds of general formula I can be obtained.

Etherification and/or esterification of free hydroxy groups is carried out according to methods that are common to one skilled in the art.

The compounds according to the invention can be present at carbon atom 17 as $\alpha,\beta$-stereoisomers. In the production of compounds according to the described processes, the compounds accumulate in most cases as mixtures of the corresponding $\alpha,\beta$-isomers. The mixtures can be separated by, for example, chromatographic processes.

According to general formula I, possible substituents can already be present in final form or in the form of a precursor even in the starting product, a substituted estrone already corresponding to the desired end product.

17-Substituents are also introduced according to known processes by nucleophilic addition of the desired substituent or a reactive precursor thereof and optionally further built up.

The estratriene-carboxylic acid esters according to the invention are produced from the corresponding hydroxy steroids analogously to processes that are also known (see, e.g., Pharmazeutische Wirkstoffe, Synthesen, Patente, Anwendungen [Pharmaceutical Active Ingredients, Syntheses, Patents, Applications]; A. Kleemann, J. Engel', Georg Thieme Verlag Stuttgart 1978. Arzneimittel, Fortschritte [Pharmaceutical Agents, Improvements] 1972 to 1985; A. Kleemann, E. Lindner, J. Engel, VCH 1987, pp. 773-814).

The estratriene-sulfamates according to the invention are available in a way that is known in the art from the corresponding hydroxy steroids by esterification with sulfamoyl chlorides in the presence of a base (Z. Chem. 1975, 15, 270-272; Steroids 1996, 61, 710-717).

Subsequent acylation of the sulfamide group results in the (N-acyl)sulfamates according to the invention, for which pharmacokinetic advantages were already detected in the case of the absence of an 8-substituent (cf. WO 97/14712).

The regioselective esterification of polyhydroxylated steroids with N-substituted and N-unsubstituted sulfamoyl chlorides is carried out according to partial protection of those hydroxyl groups that are to remain unesterified. Silyl ethers have turned out to be protective groups with selective reactivity that is suitable for this purpose, since these silyl ethers are stable under the conditions of sulfamate formation, and the sulfamate group remains intact when the silyl ethers are again cleaved off for regeneration of the residual hydroxyl group(s) still contained in the molecule (Steroids 1996, 61, 710-717).

The production of the sulfamates according to the invention with one or more additional hydroxyl groups in the molecule is also possible in that the starting material is suitable hydroxy-steroid ketones. First, depending on the goal, one or more hydroxyl groups that are present are subjected to sulfamoylation. Then, the sulfamate groups optionally can be converted with a desired acyl chloride in the presence of a base into the (N-acyl)sulfamates in question. The now present oxosulfamates or oxo-(N-acyl)sulfamates are converted by reduction into the corresponding hydroxysulfamates or hydroxy-(N-acyl)sulfamates (Steroids 1996, 61, 710-717). Sodium borohydride and the borane-dimethyl sulfide complex are suitable as proper reducing agents.

Substituents according to general formula I can also be introduced in the stage of estratrienes that are already substituted in 8-position, however. This can be useful or necessary especially in the case of multiple substitutions of the desired final compound.

The examples below are used for a more detailed explanation of the invention.

As starting material for such syntheses, 11-keto-estratetraene derivatives (U.S. Pat. No. 3,491,089, Tetrahedron Letters, 1967, 37, 3603), which are substituted stereoselectively in 8β-position in the reaction with diethylaluminum cyanide, are used. The synthesis of compound (1) is described (WO 01/77139). By conversion into a Δ-9,11-enol triflate and subsequent Sonogashira coupling, 8β-substituted 11-alkyl-estra-1,3,5(10),9(11)-tetraenes are obtained. The 8β-cyano grouping can then be converted into the 8β-aldehyde. A functionalization (e.g. by Wittig reactions), after hydrogenation of the C(9)-C(11) double bond has taken place, results in the 8β,11β-disubstituted steroids according to the invention (Diagram 1).

The 8β-substituted 11-alkyl-estra-1,3,5(10),9(11)-tetraenes that are first obtained in this sequence, just like the 8β-substituted 11β-alkyl-estra-1,3,5(10),9(11)-trienes, can be further reacted to many substitution patterns on the steroid according to the method that is known to one skilled in the art.

Frequently used abbreviations:

THP=Tetrahydropyran-2-yl;

Me=Methyl;

Bn=Benzyl;

Tf=Trifluoromethanesulfonyl;

TBS=tert-Butyldimethylsilyl;

TMS=Trimethylsilyl;

Äquiv.=Equivalent

Synthesis of 5-Benzyloxypent-1-ine 15 ml of 4-pentin-1-ol is added in drops at 0° C. to a suspension of 17.4 g of sodium hydride (55%) in 200 ml of DMF, and it is stirred for 1 hour at 0° C. Then, 30 ml of benzyl bromide is added in drops at this temperature, and it is stirred for another 2 hours at 0° C. Then, the reaction is carefully neutralized with 1N hydrochloric acid. The phase separation is carried out between diethyl ether and water, and the aqueous phase is extracted several times with diethyl ether. The combined organic phases are washed with water, saturated sodium bicarbonate solution and saturated sodium chloride solution, dried on magnesium sulfate and concentrated by evaporation. The residue is distilled in an oil pump vacuum, and 22.7 g of 5-benzyloxypent-1-ine is obtained as a colorless oil.

Synthesis of Aldehyde 9a

Diagram 1

3-Methoxy-17β-(tetrahydropyran-2-yloxy)-11-trifluoromethanesulfonyloxy-estra-1,3,5(10),9,(11)-tetraene-8-carbonitrile (2)

16 ml of trifluoromethanesulfonic acid anhydride is added in drops to a solution of 20 g of ketone 1 in 490 ml of pyridine at 0° C., and it is stirred at room temperature until the reaction is completed. Pyridine is distilled off with toluene as a co-solvent, the residue is taken up in ethyl acetate, washed with 1N hydrochloric acid, water, saturated sodium bicarbonate solution and saturated sodium chloride solution, dried on magnesium sulfate and concentrated by evaporation. The residue is filtered on silica gel (cyclohexane/ethyl acetate), and 18.12 g of triflate 2 is produced as a light yellow foam, which is used without further purification in the next stage.

11-[5-(Benzyloxy)-pent-1-inyl]-3-methoxy-17β-(tetrahydropyran-2-yloxy)-estra-1,3,5(10),9(11)-tetraene-8-carbonitrile (3)

0.75 g of palladium(II)-acetate (47%), 1.8 g of triphenylphosphine and 1.28 g of copper(I)-iodide are added in succession to a solution of 18.1 g of triflate 2 in 170 ml of piperidine, and then a solution of 11.66 g of 5-benzyloxy-pent-1-ine in 50 ml of piperidine is added in drops. The reaction solution is heated to 50° C. and stirred until the reaction is completed. For working-up, a phase separation between diethyl ether/water is carried out, and the aqueous phase is extracted several times with diethyl ether. The combined organic phases are neutralized with 1N hydrochloric acid, washed with saturated sodium bicarbonate solution and saturated sodium chloride solution, dried on magnesium sulfate and concentrated by evaporation. The residue is purified by column chromatography (cyclohexane/ethyl acetate) and yields 15.26 g of alkyne 3 as a light brown foam [LC-MS: m/z theor.: 565, pract.: 566 (M+H)$^+$].

11-[5-(Benzyloxy)-pentyl]-3-methoxy-17β-(tetrahydropyran-2-yloxy)-estra-1,3,5(10),9(11)-tetraene-8-carbonitrile (4)

A solution of 15.26 g of alkyne 3 in 300 ml of tetrahydrofuran/methanol (3:1) is mixed with 2.7 g of palladium (10% on magnesium carbonate) and stirred at room temperature under a hydrogen atmosphere (1 bar) until the reaction is completed. For working-up, it is filtered on Celite and concentrated by evaporation in a vacuum. 15.4 g of a colorless foam 4 is obtained, which is used without further purification in the next stage (GC-MS: m/z theor.: 569, pract.: 569).

11-[5-(Benzyloxy)pentyl]-17β-hydroxy-3-methoxyestra-1,3,5(10),9(11)-tetraene-8-carbaldehyde (5)

A solution that consists of 28 ml of diisobutyl aluminum hydride in 83 ml of toluene is added in drops at −10° C. to a solution of 15.4 g of nitrile 4 in 280 ml of toluene. The reaction solution is stirred at 0° C. until the reaction is completed, mixed in succession with 460 ml of toluene, 92 ml of saturated sodium bicarbonate solution, and 9 ml of 2-propanol, and it is stirred for several hours at room temperature. Then, it is filtered on Celite, and the filtrate is concentrated by evaporation. The thus obtained colorless foam is dissolved in 280 ml of ethanol/water (5:1), 28.75 g of p-toluenesulfonic acid is added, the reaction solution is heated to 60° C., and it is stirred until the reaction is completed. Then, a large portion of the ethanol is removed in a rotary evaporator, the residue is diluted with ethyl acetate, washed with water, saturated sodium bicarbonate solution and saturated sodium chloride solution, dried on magnesium sulfate and concentrated by evaporation. The residue is purified by column chromatography (cyclohexane/ethyl acetate) and yields 12.49 g of aldehyde 5 as a light brown viscous mass (GC-MS: m/z theor.: 488, pract.: 488).

11-[5-(Benzyloxy)pentyl]-17β-(tert-butyldimethylsilyloxy)-3-methoxyestra-1,3,5(10),9(11)-tetraene-8-carbaldehyde (6)

4.46 g of imidazole and 9.66 g of tert-butyldimethylsilyl chloride are added in succession at 0° C. to a solution of 12.49 g of alcohol 5 in 160 ml of N,N-dimethylformamide and stirred at room temperature until the reaction is completed. For working-up, the aqueous phase is mixed with water and extracted several times with diethyl ether. The combined organic phases are washed with water and saturated sodium chloride solution, dried on magnesium sulfate and concentrated by evaporation. The residue is purified by column chromatography (cyclohexane/ethyl acetate) and yields 14.36 g of silyl ether 6 as a yellow, viscous mass (GC-MS: m/z theor.: 602, pract.: 602).

17β-(tert-Butyldimethylsilyloxy)-11β-(5-hydroxypentyl)-3-methoxyestra-1,3,5(10)-triene-8-carbaldehyde (7)

A solution of 14.36 g of tetraene 6 in 400 ml of tetrahydrofuran/methanol (3:1) is mixed with 2.8 g of palladium (10% on carbon) and stirred under a hydrogen atmosphere (100 bar) for two days at room temperature. This reaction is repeated twice. For working-up, it is filtered on Celite and concentrated by evaporation in a vacuum. The residue is purified by column chromatography (cyclohexane/ethyl acetate) and yields 8.25 g of 7 as a colorless foam (GC-MS: m/z theor.: 514, pract.: 514).

General Operating Instructions for Wittig Olefination of Estratriene-8-carbaldehydes A suspension that consists of sodium hydride (80%, 15 equivalents) in dimethyl sulfoxide (0.5 ml/mmol) is heated for 1 hour to 70° C. Then, a solution of the corresponding alkyltriphenylphosphonium bromide (15 equivalents) in dimethyl sulfoxide (2 ml/mmol) is added in drops at room temperature. The reaction solution is colored yellowish-green and is stirred for another hour at room temperature.

A solution of the corresponding 8-carbaldehyde in dimethyl sulfoxide (5 ml/mmol) is added in drops at room temperature to the solution of the ylide. The reaction solution is stirred at 40° C. until the reaction is completed, cooled to 0° C. and mixed with water. Then, it is extracted several times with diethyl ether, the combined organic phases are washed with water and saturated sodium chloride solution, dried on magnesium sulfate and concentrated by evaporation. Column-chromatographic purification (cyclohexane/ethyl acetate) yields the corresponding olefins.

17β-tert.-Butyldimethylsilyloxy-11β-(5-hydroxypentyl)-3-methoxy-8-vinyl-estra-1,3,5(10)-triene (8)

Analogously to the general olefination instructions, 4 g of aldehyde 7 in the reaction with methyltriphenylphosphonium bromide yields 3.62 g of olefin 8 as a colorless foam (GC-MS: m/z theor.: 512, pract.: 512).

5-[17β-(tert-Butyldimethylsilyloxy)-3-methoxy-8-vinylestra-1,3,5(10)-trien-11β-yl]valeraldehyde (9a)

1.24 g of pyridinium chlorochromate is introduced into 9 ml of dichloromethane, a solution of 1.5 g of alcohol 8 in 15 ml of dichloromethane is added in drops, and then 940 mg of Celite is added. The reaction mixture is stirred at room temperature until the reaction is completed, concentrated by evaporation in a rotary evaporator, then taken up in diethyl ether and filtered on silica gel. This yields 1.41 g of aldehyde 9a as a light yellow, viscous mass (GC-MS: m/z theor.: 510, pract.: 510), which is used without further purification in the subsequent reaction.

Synthesis of Aldehyde 9b

Diagram 2

11β-(5-Bromopentyl)-17β-tert.-butyldimethylsilyloxy-3-methoxy-8-vinyl-estra-1,3,5(10)-triene (10)

1.62 g of triphenylphosphine and 420 mg of imidazole are added in succession to a solution of 2.11 g of alcohol 8 in 41 ml of dichloromethane. The solution is cooled to 0° C., and 2.05 g of tetrabromomethane is added. The reaction mixture is heated to room temperature and stirred until the reaction is completed. For working-up, it is diluted with dichloromethane, the organic phase is washed with water and saturated sodium chloride solution, dried on magnesium sulfate and concentrated by evaporation. Column-chromatographic purification (cyclohexane/ethyl acetate) yields 2.3 g of bromide 10 as a colorless, viscous mass (GC-MS: m/z theor.: 574, pract.: 574).

6-[17β-(tert-Butyldimethylsilyloxy)-3-methoxy-8-vinylestra-1,3,5(10)-trien-11β-yl]capronitrile (11a)

295 mg of sodium cyanide and a catalytic amount of sodium iodide are added to a solution of 2.3 g of bromide 10 in 20 ml of N,N-dimethylformamide. The reaction mixture is stirred at room temperature until the reaction is completed. For working-up, it is diluted with diethyl ether, the organic phase is washed with water and saturated sodium chloride solution, dried on magnesium sulfate and concentrated by evaporation. This yields 1.97 g of cyanide 11 as a colorless foam, which is used without further purification in the next stage (GC-MS: m/z theor.: 521, pract.: 521).

6-[17β-(tert-Butyldimethylsilyloxy)-3-methoxy-8-vinylestra-1,3,5(10)-trien-11β-yl]capronaldehyde (9b)

A solution that consists of 1 ml of diisobutylaluminium hydride in 1 ml of toluene is added in drops at −10° C. to a solution of 1.16 g of cyanide 11a in 23 ml of toluene. The reaction solution is stirred at −10° C. until the reaction is completed, mixed in succession with 17 ml of toluene, 6 ml of saturated sodium bicarbonate solution and 0.7 ml of 2-propanol and stirred for several hours at room temperature. Then, it is filtered on Celite, and the filtrate is concentrated by evaporation. Column-chromatographic purification (cyclohexane/ethyl acetate) yields 1.13 g of aldehyde 9b as a colorless foam (GC-MS: m/z theor.: 524, pract.: 524).

Synthesis of Bromide 13

Diagram 2

17β-tert.-Butyldimethylsilyloxy-11β-(6-hydroxyhexyl)-3-methoxy-8-vinyl-estra-1,3,5(10)-triene (12)

282 mg of sodium borohydride is added at 0° C. to a solution of 1.95 g of aldehyde 9b in 37 ml of tetrahydrofuran/methanol (1:1). The reaction solution is stirred at room temperature until the reaction is completed. For working-up, it is diluted with diethyl ether, the organic phase is washed with 1N hydrochloric acid, water, saturated sodium bicarbonate solution and saturated sodium chloride solution, dried on magnesium sulfate and concentrated by evaporation. Column-chromatographic purification (cyclohexane/ethyl acetate) yields 1.06 g of alcohol 12 as a colorless, viscous mass (GC-MS: m/z theor.: 526, pract.: 526).

11β-(6-Bromohexyl)-17β-tert.-butyldimethylsilyloxy-3-methoxy-8-vinyl-estra-1,3,5(10)-triene (13)

The reaction of 930 mg of alcohol 12 is carried out analogously to the test instructions for the conversion of alcohol 8 into bromide 10. In this way, 975 mg of bromide 13 is obtained as a colorless, viscous oil (GC-MS: m/z theor.: 588, pract.: 588).

Synthesis of Aldehyde 9c

Diagram 3

7-[17β-(tert-Butyldimethylsilyloxy)-3-methoxy-8-vinylestra-1,3,5(10)-trien-11β-yl]heptanitrile (11b)

The synthesis of (cyanomethyl)trimethylphosphonium iodide is carried out in very much the same way as the procedure described in the literature [*J. Org. Chem.* 2001, 66, 2518-2521] from trimethylphosphine and iodoacetonitrile.

2.42 g of (cyanomethyl)trimethylphosphonium iodide is added to a solution of 1 g of alcohol 8 in 18 ml of propionitrile, and then 2.1 ml of diisopropyl ethylamine is added in drops. The reaction mixture is stirred for 14 hours at 97° C. After cooling to room temperature, the batch is mixed with 10 ml of water and 1 ml of concentrated hydrochloric acid. The phase separation is carried out between ethyl acetate/water. The organic phase is washed with water and saturated sodium chloride solution, dried on magnesium sulfate and concentrated by evaporation. Column-chromatographic purification (cyclohexane/ethyl acetate) yields 480 mg of cyanide 11b as a colorless foam (GC-MS: m/z theor.: 535, pract.: 535).

7-[17β-(tert-Butyldimethylsilyloxy)-3-methoxy-8-vinylestra-1,3,5(10)-trien-11β-yl]heptanal (9c)

A solution that consists of 0.4 ml of diisobutyl aluminum hydride in 0.4 ml of toluene is added in drops at −10° C. to a solution of 480 mg of cyanide 11b in 10 ml of toluene. The reaction solution is stirred at −10° C. until the reaction is completed, mixed in succession with 8 ml of toluene, 3 ml of saturated sodium bicarbonate solution and 0.3 ml of 2-propanol, and stirred for several hours at room temperature. Then, it is filtered on Celite, and the filtrate is concentrated by evaporation. Column-chromatographic purification (cyclohexane/ethyl acetate) yields 361 mg of aldehyde 9c as a colorless foam (GC-MS: m/z theor.: 538, pract.: 538).

EXAMPLE 1

General Operating Instructions for Reaction of Aldehydes 9a-c with (Perfluoroalkyl)-trimethylsilanes and Subsequent Cleavage of the Trimethylsilyl Ether with Tetrabutylammonium Fluoride-Trihydrate (Diagrams 4-5)

A catalytic amount of tetrabutylammonium fluoride-trihydrate is added to a solution of the corresponding carbonyl compound (1 equivalent) in tetrahydrofuran (2 ml/mmol), the solution is cooled to −20° C., and the (perfluoroalkyl)-trimethylsilane (15 equivalents) is added in drops. The cold bath is removed, and the reaction solution is stirred at room temperature until the reaction is completed. For working-up, it is diluted with diethyl ether, the organic phase is washed with water and saturated sodium chloride solution, dried on magnesium sulfate and concentrated by evaporation. The thus obtained trimethylsilyl ether proves partially unstable in the subsequent column-chromatographic purification and is reacted in a mixture with its corresponding alcohol. To this end, the mixture is dissolved in tetrahydrofuran (10 ml/mmol), mixed at room temperature with tetrabutylammonium fluoride-trihydrate (1.5 equivalents) and stirred at room temperature until the reaction is completed. For working-up, it is diluted with diethyl ether, the organic phase is washed with water and saturated sodium chloride solution, dried on magnesium sulfate and concentrated by evaporation. Column-chromatographic purification (cyclohexane/ethyl acetate) yields the corresponding perfluoroalkyl-substituted alcohols as colorless foams.

17β-tert.-Butyldimethylsilyloxy-3-methoxy-11β-[(R/S)-6,6,6-trifluoro-5-hydroxyhexyl]-8-vinyl-estra-1,3,5(10)-triene (14a)

In the reaction with (trifluoromethyl)-trimethylsilane analogously to instructions 1.1, 900 mg of aldehyde 9a yields 804 mg of alcohol 14a as a colorless foam (GC-MS: m/z theor.: 580, pract.: 580) and a mixture of its diastereomers.

General Operating Instructions for Simultaneous Cleavage of tert-Butyldimethylsilyl Ether and Methyl Ether by Means of Boron Trichloride/Tetrabutylammonium Iodide (Diagrams 2-8)

A corresponding amount of boron trichloride (1.5 equivalents each of ether that is to be cleaved, one additional equivalent for each basic grouping) is added in drops to a solution, cooled to −78° C., of the corresponding steroid and tetrabutylammonium iodide (1.5 equivalents each of the ether to be cleaved, one additional equivalent for each basic grouping) in dichloromethane (5 ml/mmol). The reaction solution is slowly heated to 0° C. and stirred until the reaction is completed. For working-up, the batch is mixed with ice water and stirred for about 30 more minutes, then it is mixed with saturated sodium bicarbonate solution and extracted several times with dichloromethane. The combined organic phases are dried with magnesium sulfate and concentrated by evaporation. The residue that is obtained is purified by column chromatography and yields the corresponding estradiols.

11β-[(R/S)-6,6,6-Trifluoro-5-hydroxyhexyl]-8-vinyl-estra-1,3,5(10)-triene-3,17β-diol (15a D1/2)

In the reaction analogously to instructions 1.2, 100 mg of steroid 14a yields 78 mg of a light yellow viscous mass that turned out to be 3-methyl ether. The 3-methyl ether is then dissolved in 2.7 ml of toluene, the solution is cooled to 0° C., and 0.5 ml of diisobutylaluminium hydride is added in drops. The reaction solution is refluxed until the reaction is completed. For working-up, the solution is cooled to 0° C., and ethanol (1 ml), ethanol/water (1:1, 2 ml), and semiconcentrated hydrochloric acid (2 ml) are added in drops in succession. The phase separation is carried out between diethyl ether/water, and the aqueous phase is extracted several times with diethyl ether. The combined organic phases are washed with water and saturated sodium chloride solution, dried on magnesium sulfate and concentrated by evaporation. Column-chromatographic purification (cyclohexane/ethyl acetate) yields 62 mg of estratrienediol 15a as a colorless, viscous mass (GC-MS: m/z theor.: 452, pract.: 452) and a mixture of its diastereomers D1/D2.

Diastereomer separation is carried out by means of preparative HPLC (Chiralpak AD 250×10, n-heptane/2-propanol 9/1 v/v, 4.7 ml/min) and in each case yields 16 mg of the two diastereomers 15a D1 ($[α]_D$=66°, chloroform) and 15a D2 ($[α]_D$=33°, chloroform).

By means of x-ray structural analysis, the R-configuration was assigned to diastereomer 15aD1, and the S-configuration at the epimeric center was assigned to diastereomer 15aD2.

EXAMPLE 2

17β-tert.-Butyldimethylsilyloxy-3-methoxy-11β-[(R/S)-7,7,7-trifluoro-6-hydroxyheptyl]-8-vinyl-estra-1,3,5(10)-triene (14b)

In the reaction with (trifluoromethyl)-trimethylsilane analogously to instructions 1.1, 500 mg of aldehyde 9b yields 292 mg of alcohol 14b as a colorless foam (GC-MS: m/z theor.: 594, pract.: 594) and a mixture of its diastereomers.

11β-[(R/S)-7,7,7-Trifluoro-6-hydroxyheptyl]-8-vinyl-estra-1,3,5(10)-triene-3,17β-diol (15b D1/2)

In the reaction analogously to instructions 1.2, 90 mg of steroid 14b yields 56 mg of estratrienediol 15b as a colorless foam (GC-MS: m/z theor.: 466, pract.: 466) and a mixture of its diastereomers D1/D2. Diastereomer separation is carried out by means of preparative HPLC (Chiralcel OD 250×51, n-hexane/2-propanol 9/1 v/v, 100 ml/min) and yields 9 mg of diastereomer 15b D1 and 7 mg of diastereomer 15b D2.

EXAMPLE 3

17β-tert-Butyldimethylsilyloxy-3-methoxy-11β-[(R/S)-8,8,8-trifluoro-7-hydroxyoctyl]-8-vinyl-estra-1,3,5(10)-triene (14c)

In the reaction with (trifluoromethyl)-trimethylsilane analogously to instructions 1.1, 360 mg of aldehyde 9c yields 370 mg of alcohol 14c as a colorless foam (GC-MS: m/z theor.: 608, pract.: 608) and a mixture of its diastereomers.

11β-[(R/S)-8,8,8-Trifluoro-7-hydroxyoctyl]-8-vinyl-estra-1,3,5(10)-triene-3,17β-diol (15c D1/2)

In the reaction analogously to instructions 1.2, 90 mg of steroid 14c yields 78 mg of estratrienediol 15c as a colorless foam (GC-MS: m/z theor.: 466, pract.: 466) and a mixture of its diastereomers D1/2. Diastereomer separation is carried out by means of preparative HPLC (Chiralpak AD 250×60, n-hexane/ethanol 95/5 v/v, 80 ml/min) and yields 23 mg of diastereomer 15c D1 and 17 mg of diastereomer 15c D2.

EXAMPLE 4

General Operating Instructions for Oxidation of the Trifluoromethyl-Substituted Alcohols (Diagram 4)

A solution of the corresponding alcohol (1 equivalent) in dichloromethane (15 ml/mmol) is added in drops at room temperature to a suspension that consists of Dess-Martin-periodinane (6 equivalents) in dichloromethane (5 ml/mmol), and it is stirred until the reaction is completed. Then, the reaction mixture is mixed with water and stirred for about 30 more minutes. The phase separation is carried out between diethyl ether/water, and the aqueous phase is extracted several times with diethyl ether. The combined organic phases are washed with saturated sodium thiosulfate, saturated sodium bicarbonate solution, water and saturated sodium chloride solution, dried on magnesium sulfate and concentrated by evaporation. Column-chromatographic purification (cyclohexane/ethyl acetate) yields the corresponding ketones.

6-[17β-(tert-Butyldimethylsilyloxy)-3-methoxy-8-vinylestra-1,3,5(10)-trien-11β-yl]-1,1,1-trifluoro-hexan-2-one (16a)

In the reaction analogously to instructions 4.1, 312 mg of alcohol 14a yields 252 mg of ketone 16a as a yellow, viscous mass (GC-MS: m/z theor.: 578, pract.: 578).

17β-tert.-Butyldimethylsilyloxy-3-methoxy-11β-[6,6,6-trifluoro-5-trifluoromethyl-5-(trimethylsilyloxy)hexyl]-8-vinyl-estra-1,3,5(10)-triene (17a)

In the reaction with (trifluoromethyl)-trimethylsilane analogously to instructions 1.1, 200 mg of alcohol 16a yields 200 mg of the column-chromatographically stable trimethylsilyl ether 17a as a light yellow, viscous mass (GC-MS: m/z theor.: 720, pract.: 720). The latter is, without the reaction with tetrabutylammonium fluoride-trihydrate being performed, used in the next stage.

11β-[6,6,6-Trifluoro-5-hydroxy-5-(trifluoromethyl)hexyl]-8-vinyl-estra-1,3,5(10)-triene-3,17β-diol (18a)

In the reaction analogously to instructions 1.2, 200 mg of steroid 17a yields 19 mg of estratrienediol 18a as a colorless foam (GC-MS: m/z theor.: 520, pract.: 520) together with 46 mg of the unreacted trimethylsilyl ether that accumulates as a by-product, which is converted by means of reaction with tetrabutylammonium fluoride-trihydrate into tetrahydrofuran (cf. instructions 1.1/trimethylsilyl ether cleavage) into compound 18a (33 mg).

EXAMPLE 5

7-[17β-(tert-Butyldimethylsilyloxy)-3-methoxy-8-vinylestra-1,3,5(10)-trien-11β-yl]-1,1,1-trifluoroheptan-2-one (16b)

In the reaction analogously to instructions 4.1, 182 mg of alcohol 14b yields 131 mg of ketone 16b as a yellow, viscous mass (GC-MS: m/z theor.: 592, pract.: 592).

17β-tert.-Butyldimethylsilyloxy-3-methoxy-11β-[7,7,7-trifluoro-6-trifluoromethyl-6-(trimethylsilyloxy)heptyl]-8-vinyl-estra-1,3,5(10)-triene (17b)

In the reaction with (trifluoromethyl)-trimethylsilane analogously to instructions 1.1, 131 mg of alcohol 16b yields 162 mg of trimethylsilyl ether 17b as a yellow, viscous mass (GC-MS: m/z theor.: 734, pract.: 734). The latter is, without performing the reaction with tetrabutylammonium fluoride-trihydrate, used in the next stage.

11β-[7,7,7-Trifluoro-6-hydroxy-6-(trifluoromethyl)heptyl]-8-vinyl-estra-1,3,5(10)-triene-3,17β-diol (18b)

In the reaction analogously to instructions 1.2, 161 mg of steroid 17b yields 57 mg of the unreacted trimethylsilyl ether. In the reaction with tetrabutylammonium fluoride-trihydrate in tetrahydrofuran (cf. instructions 1.1/trimethylsily ether cleavage), 37 mg of the trimethylsilyl ether yields 20 mg of estratrienediol 18b as a colorless foam (GC-MS: m/z theor.: 534, pract.: 534).

EXAMPLE 6

8-[17β-(tert-Butyldimethylsilyloxy)-3-methoxy-8-vinylestra-1,3,5(10)-trien-11β-yl]-1,1,1-trifluorooctan-2-one (16c)

In the reaction analogously to instructions 4.1, 200 mg of alcohol 14c yields 138 mg of ketone 16c as a yellow, viscous mass (GC-MS: m/z theor.: 606, pract.: 606).

17β-tert-Butyldimethylsilyloxy-3-methoxy-11β-[8,8,8-trifluoro-7-trifluoromethyl-7-(trimethylsilyloxy)octyl]-8-vinyl-estra-1,3,5(10)-triene (17c)

In the reaction with (trifluoromethyl)-trimethylsilane analogously to instructions 1.1, 135 mg of alcohol 16c yields 159 mg of trimethylsilyl ether 17c as a yellow, viscous mass (GC-MS: m/z theor.: 748, pract.: 748). The latter is, without the reaction being performed with tetrabutylammonium fluoride-trihydrate, used in the next stage.

11β-[8,8,8-Trifluoro-7-hydroxy-7-(trifluoromethyl)octyl]-8-vinyl-estra-1,3,5(10)-triene-3,17β-diol (18c)

In the reaction analogously to instructions 1.2, 155 mg of steroid 17c yields 57 mg of the unreacted trimethylsilyl ether, which in the reaction with tetrabutylammonium fluoride-trihydrate in tetrahydrofuran (cf. instructions 1.1/trimethylsilyl ether cleavage) yields 45 mg of estratrienediol 18c as a colorless foam (GC-MS: m/z theor.: 548, pract.: 548).

EXAMPLE 7

General Operating Instructions for the Reaction of Aldehydes 9a-b with Pentafluoroethyl Lithium (Diagram 5)

nButyllithium (1.6 M in hexane, 1 equivalent) is added in drops at −78° C. to a 1 M solution of pentafluoroethyl iodide (10 equivalents in reference to the carbonyl compound), and the solution is stirred for 1 hour at −78° C. Then, at this temperature, a solution of the corresponding carbonyl compound in tetrahydrofuran (5 ml/mmol) is added in drops. The reaction solution is slowly heated and stirred until the conversion is completed. For working-up, the reaction solution is mixed with saturated ammonium chloride solution and extracted several times with diethyl ether. The combined organic phases are washed with water and saturated sodium chloride solution, dried on magnesium sulfate and concentrated by evaporation. Column-chromatographic purification (cyclohexane/ethyl acetate) yields the corresponding pentafluoroethyl-substituted alcohols.

17β-tert.-Butyldimethylsilyloxy-3-methoxy-11β-[(R/S)-7,7,7,6,6-pentafluoro-5-hydroxyheptyl]-8-vinyl-estra-1,3,5(10)-triene (19a)

In the reaction analogously to instructions 7.1, 55 mg of aldehyde 9a yields 61 mg of alcohol 19a as a colorless foam (GC-MS: m/z theor.: 630, pract.: 630) and a mixture of its diastereomers.

11β-[(R/S)-7,7,7,6,6-Pentafluoro-5-hydroxyheptyl]-8-vinyl-estra-1,3,5(10)-triene-3,17β-diol (20a D1/2)

In the reaction analogously to instructions 1.2, 60 mg of steroid 19a yields 26 mg of estratrienediol 20a D1/2 as a colorless foam (GC-MS: m/z theor.: 502, pract.: 502) and a mixture of its diastereomers.

EXAMPLE 8

17β-tert.-Butyldimethylsilyloxy-3-methoxy-11β-[(R/S)-8,8,8,7,7-pentafluoro-6-hydroxyoctyl]-8-vinyl-estra-1,3,5(10)-triene (19b)

In the reaction analogously to instructions 7.1, 45 mg of aldehyde 9b yields 47 mg of alcohol 19b as a colorless foam (GC-MS: m/z theor.: 644, pract.: 644) and a mixture of its diastereomers.

11β-[(R/S)-8,8,8,7,7-Pentafluoro-6-hydroxyoctyl]-8-vinyl-estra-1,3,5(10)-triene-3,17β-diol (20b D1/2)

In the reaction analogously to instructions 1.2, 45 mg of steroid 19b yields 16 mg of estratrienediol 20b D1/2 as a colorless foam (GC-MS: m/z theor.: 516, pract.: 516) and a mixture of its diastereomers.

EXAMPLE 9

17β-tert.-Butyldimethylsilyloxy-11β-[(R/S)-8,8,8,7,7,6,6-heptafluoro-5-trimethylsilyloxyoctyl]-3-methoxy-8-vinyl-estra-1,3,5(10)-triene (21a)

In the reaction with (heptafluoropropyl)-trimethylsilane analogously to instructions 1.1, 60 mg of aldehyde 9a yields 81 mg of the stable trimethylsilyl ether 21a as a colorless foam (GC-MS: m/z theor.: 752, pract.: 752) and a mixture of its diastereomers. The latter is, without performing the reaction with tetrabutylammonium fluoride-trihydrate, used in the next stage.

11β-[(R/S)-8,8,8,7,7,6,6-Heptafluoro-5-hydroxyoctyl]-8-vinyl-estra-1,3,5(10)-triene-3,17β-diol (22a D1/2)

In the reaction analogously to instructions 1.2, 80 mg of steroid 21a yields 27 mg of estratrienediol 22a D1/2 as a colorless foam (GC-MS: m/z theor.: 552, pract.: 552) and a mixture of its diastereomers.

EXAMPLE 10

17β-tert.-Butyldimethylsilyloxy-11β-[(R/S)-9,9,9,8,8,7,7-heptafluoro-6-trimethylsilyloxynonyl]-3-methoxy-8-vinyl-estra-1,3,5(10)-triene (21b)

In the reaction with (heptafluoropropyl)-trimethylsilane analogously to instructions 1.1, 70 mg of aldehyde 9b yields 94 mg of the stable trimethylsilyl ether 21b as a colorless foam (GC-MS: m/z theor.: 766, pract.: 766) and a mixture of its diastereomers. The latter is, without performing the reaction with tetrabutylammonium fluoride-trihydrate, used in the next stage.

11β-[(R/S)-9,9,9,8,8,7,7-Heptafluoro-6-hydroxynonyl]-8-vinyl-estra-1,3,5(10)-triene-3,17β-diol (22b D1/2)

In the reaction analogously to instructions 1.2, 94 mg of steroid 21b yields 41 mg of estratrienediol 22b D1/2 as a colorless foam (GC-MS: m/z theor.: 566, pract.: 566) and a mixture of its diastereomers.

EXAMPLE 11

17β-tert-Butyldimethylsilyloxy-3-methoxy-11β-[(R/S)-7,7,6-trifluoro-5-trimethylsilyloxyhept-6-enyl]-8-vinyl-estra-1,3,5(10)-triene (23a)

The synthesis of 1,1,2-trifluoro-2-trimethylsilylethylene is carried out in very much the same way as the procedure that is described in the literature [*J. Fluorine Chem.* 2003, 121, 75-77] from 1-bromo-1,2,2-trifluoroethene, zinc, and trimethylsilyl chloride.

In the reaction with 1,1,2-trifluoro-2-trimethylsilyl ethylene analogously to instructions 1.1, 60 mg of aldehyde 9a yields 77 mg of trimethylsilyl ether 23a as a colorless foam (GC-MS: m/z theor.: 664, pract.: 664) and a mixture of its diastereomers. The latter is used without further purification in the next stage.

11β-[(R/S)-7,7,6-Trifluoro-5-hydroxyhept-6-enyl]-8-vinyl-estra-1,3,5(10)-triene-3,17β-diol (24a D1/2)

0.16 ml of 10% hydrochloric acid is added at room temperature to a solution of 77 mg of silyl ether 23a in 4 ml of acetone. The reaction solution is stirred at room temperature until the reaction is completed and mixed with saturated sodium bicarbonate solution. The phase separation is carried out between ethyl acetate/water. The organic phase is washed with saturated sodium chloride solution, dried on magnesium sulfate and concentrated by evaporation. The thus obtained residue is filtered on silica gel (cyclohexane/ ethyl acetate) and again concentrated by evaporation. The colorless foam that is obtained is dissolved in 1 ml of toluene, 0.15 ml of diisobutyl aluminum hydride is added in drops at 0° C., and the reaction solution is refluxed until conversion is completed. After cooling to 0° C., the reaction mixture is mixed in succession with 0.5 ml of ethanol, 0.5 ml of ethanol/water (1:1) and 0.5 ml of semi-concentrated hydrochloric acid and stirred for about 30 more minutes. The phase separation is carried out between diethyl ether/water. The organic phase is washed with saturated sodium chloride solution, dried on magnesium sulfate and concentrated by evaporation. Column-chromatographic purification (cyclohexane/ethyl acetate) yields 14 mg of estratrienediol 24a D1/2 as a colorless foam (GC-MS: m/z theor.: 464, pract.: 464) and a mixture of its diastereomers.

EXAMPLE 12

17β-tert-Butyldimethylsilyloxy-3-methoxy-11β-[(R/S)-8,8,7-trifluoro-6-trimethylsilyloxyoct-7-enyl]-8-vinyl-estra-1,3,5(10)-triene (23b)

In the reaction with 1,1,2-trifluoro-2-trimethylsilyl ethylene analogously to instructions 1.1, 80 mg of aldehyde 9b yields 95 mg of trimethylsilyl ether 23b as a colorless foam (GC-MS: m/z theor.: 678, pract.: 678) and a mixture of its diastereomers. The latter is used without further purification in the next stage.

11β-[(R/S)-8,8,7-Trifluoro-6-hydroxyoct-7-enyl]-8-vinyl-estra-1,3,5(10)-triene-3,17β-diol (24b D1/2)

In the reaction analogously to instructions 11.2, 95 mg of aldehyde 23b yields 22 mg of the trimethylsilyl ether 24b D1/2 as a colorless foam (GC-MS: m/z theor.: 478, pract.: 478) and a mixture of its diastereomers.

EXAMPLE 13

General Operating Instructions for the Reaction of an Aldehyde or Ketone with Methyl Lithium Excess methyl lithium (5-10 equivalents, 1.6 M in diethyl ether) is added in drops to a solution, cooled to −78° C., of the corresponding carbonyl compound (I equivalent) in tetrahydrofuran (10 ml/mmol), and the reaction solution is stirred at this temperature until the reaction is completed. For working-up, the reaction solution is mixed with saturated ammonium chloride solution/water/diethyl ether, the organic phase is washed with water and saturated sodium chloride solution, dried on magnesium sulfate and concentrated by evaporation. Column-chromatographic purification (cyclohexane/ethyl acetate) yields the corresponding methyl-substituted alcohols as colorless foams.

17β-tert-Butyldimethylsilyloxy-11β-[R/S)-5-hydroxyhexyl]-3-methoxy-8-vinyl-estra-1,3,5(10)-triene (25a)

In the reaction analogously to instructions 13.1, 200 mg of aldehyde 9a yields 120 mg of alcohol 25a as a colorless foam (GC-MS: m/z theor.: 526, pract.: 526) and a mixture of its diastereomers.

11β-[(R/S)-5-Hydroxyhexyl]-8-vinyl-estra-1,3,5 (10)-triene-3,17β-diol (26a D1/2)

In the reaction analogously to instructions 1.2, 25 mg of steroid 25a yields 8 mg of estratrienediol 26a D1/2 as a colorless foam (GC-MS: m/z theor.: 398, pract.: 398) and a mixture of its diastereomers.

EXAMPLE 14

17β-tert-Butyldimethylsilyloxy-11β-[(R/S)-6-hydroxyheptyl]-3-methoxy-8-vinyl-estra-1,3,5(10)-triene (25b)

In the reaction analogously to instructions 13.1, 155 mg of aldehyde 9b yields 100 mg of alcohol 25b as a colorless foam (GC-MS: m/z theor.: 540, pract.: 540) and a mixture of its diastereomers.

11β-[(R/S)-6-Hydroxyheptyl]-8-vinyl-estra-1,3,5 (10)-triene-3,17β-diol (26b D1/2)

In the reaction analogously to instructions 1.2, 25 mg of steroid 25b yields 10 mg of estratrienediol 26b D1/2 as a colorless foam (GC-MS: m/z theor.: 412, pract.: 412) and a mixture of its diastereomers.

EXAMPLE 15

6-[17β-(tert-Butyldimethylsilyloxy)-3-methoxy-8-vinylestra-1,3,5(10)-trien-11β-yl]-hexane-2-one (27a)

58 mg of pyridinium chlorochromate and 58 mg of Celite are introduced into 0.5 ml of dichloromethane, a solution of 95 mg of alcohol 25a in 0.9 ml of dichloromethane is added in drops, and the reaction mixture is stirred at room temperature until the reaction is completed. Then, the reaction mixture is filtered on Celite and silica gel, and the filtrate is concentrated by evaporation. This yields 81 mg of ketone 27a as a light yellow, viscous mass (GC-MS: m/z theor.: 524, pract.: 524), which is used without further purification in the reaction below.

17β-tert-Butyldimethylsilyloxy-3-methoxy-11β-[5-methyl-5-hydroxyhexyl]-8-vinyl-estra-1,3,5(10)-triene (28a)

In the reaction analogously to instructions 13.1, 75 mg of ketone 27a yields 45 mg of alcohol 28a as a colorless foam (GC-MS: m/z theor.: 540, pract.: 540).

11β-[5-Methyl-5-hydroxyhexyl]-8-vinyl-estra-1,3,5 (10)-triene-3,17β-diol (29a)

In the reaction analogously to instructions 1.2, 40 mg of steroid 28a yields 22 mg of estratrienediol 29a as a colorless foam (GC-MS: m/z theor.: 412, pract.: 412).

EXAMPLE 16

7-[17β-(tert-Butyldimethylsilyloxy)-3-methoxy-8-vinylestra-1,3,5(10)-trien-11β-yl]-heptan-2-one (27b)

In the reaction analogously to instructions 15.1, 70 mg of alcohol 25b yields 56 mg of ketone 27b as a yellow foam (GC-MS: m/z theor.: 538, pract.: 538), which is used without further purification in the reaction below.

17β-tert-Butyldimethylsilyloxy-3-methoxy-11β-[6-methyl-6-hydroxyheptyl]-8-vinyl-estra-1,3,5(10)-triene (28b)

In the reaction analogously to instructions 13.1, 53 mg of ketone 27b yields 30 mg of alcohol 28b as a colorless foam (GC-MS: m/z theor.: 554, pract.: 554).

11β-[6-Methyl-6-hydroxyheptyl]-8-vinyl-estra-1,3,5 (10)-triene-3,17β-diol (29b)

In the reaction analogously to instructions 1.2, 26 mg of steroid 28b yields 9 mg of estratrienediol 29b as a colorless foam (GC-MS: m/z theor.: 426, pract.: 426).

EXAMPLE 17

11β-(5-Bromopentyl)-8-vinyl-estra-1,3,5(10)-triene-3,17β-diol (30a)

In the reaction analogously to instructions 1.2, 1.55 g of steroid 10 yields 836 mg of estratrienediol 30a as a colorless foam (GC-MS: m/z theor.: 446, pract.: 446).

General Operating Instructions for Introducing an Amino Grouping (Diagram 7)

A corresponding amount of bromide is dissolved in N,N-dimethylformamide (5 ml/mmol), mixed with an excess of the corresponding amine and stirred at room temperature (optionally at 40° C.) until the reaction is completed. The phase separation is carried out between ethyl acetate/water, and the aqueous phase is extracted several times with ethyl acetate. The organic phase is washed with water and saturated sodium chloride solution, dried with magnesium sulfate and concentrated by evaporation. The column-chromatographic purification is carried out on silica gel with an ethyl acetate/methanol mixture as an eluant, and yields the corresponding amines.

11β-[5-(Methylamino)pentyl]-8-vinylestra-1,3,5 (10)-triene-3,17β-diol (31a)

In the reaction with methylamine (40% in water, 2 ml/mmol) analogously to instructions 17.2, 258 mg of bromide 30a yields 161 mg of amine 31a as a colorless solid (GC-MS: m/z theor.: 397, pract.: 397).

EXAMPLE 18

11β-[5-(Dimethylamino)pentyl]-8-vinylestra-1,3,5 (10)-triene-3,17β-diol (32a)

In the reaction with dimethylamine (2 M in tetrahydrofuran, 10 equivalents) analogously to instructions 17.2, 30 mg of bromide 30a yields 12 mg of amine 32a as a colorless foam (GC-MS: m/z theor.: 411, pract.: 411).

EXAMPLE 19

11β-[5-(Pyrrolidin-1-yl)pentyl]-8-vinylestra-1,3,5 (10)-triene-3,17β-diol (33a)

In the reaction with pyrrolidine (10 equivalents) analogously to instructions

EXAMPLE 20

11β-[5-(1-Piperidyl)pentyl]-8-vinylestra-1,3,5(10)-triene-3,17β-diol (34a)

In the reaction with piperidine (10 equivalents) analogously to instructions 17.2, 50 mg of bromide 30a yields 41 mg of amine 34a as a colorless foam (GC-MS: m/z theor.: 451, pract.: 451).

EXAMPLE 21

11β-(5-Morpholinopentyl)-8-vinylestra-1,3,5(10)-triene-3,17β-diol (35a)

In the reaction with morpholine (10 equivalents) analogously to instructions 17.2, 30 mg of bromide 30a yields 10 mg of amine 35a as a colorless foam (GC-MS: m/z theor.: 453, pract.: 453).

EXAMPLE 22

General Operating Instructions for Introducing a Polyfluorinated Alkyl Chain into Amines 31a-b (Diagram 7)

A corresponding amount of amine is dissolved in N,N-dimethylformamide (5 ml/mmol), a solution of the corresponding tosylate (1.5 equivalents) in N,N-dimethylformamide (5 ml/mmol) is added in drops, and 20 equivalents of sodium carbonate is added. Then, the reaction mixture is stirred for 8 hours at 40° C. For working-up, a phase separation between ethyl acetate/water and the aqueous phase is extracted several times with ethyl acetate. The organic phase is washed with water and saturated sodium chloride solution, dried with magnesium sulfate and concentrated by evaporation. The column-chromatographic purification is carried out on silica gel with a chloroform/methanol mixture as an eluant and in addition to unreacted starting material yields the corresponding tertiary amines.

11β-{5-[Methyl(8,8,9,9,9-pentafluorononyl)amino]pentyl}-8-vinylestra-1,3,5(10)-triene-3,17β-diol (36a)

In the reaction with 8,8,9,9,9-pentafluorononyltosylate analogously to instructions 22.1, 32 mg of amine 31a yields 16 mg of amine 36a as colorless crystals (GC-MS: m/z theor.: 613, pract.: 613).

EXAMPLE 23

11β-{5-[(7,7,8,8,9,9,9-Heptafluorononyl)methylamino]pentyl}-8-vinylestra-1,3,5(10)-triene-3,17β-diol (37a)

In the reaction with 7,7,8,8,9,9,9-heptafluorononyltosylate analogously to instructions 22.1, 31 mg of amine 31a yields 22 mg of amine 37a as colorless crystals (GC-MS: m/z theor.: 649, pract.: 649).

EXAMPLE 24

General Instructions for Acylation of Amines 31a-b (Diagram 7)

A corresponding amount of amine is dissolved in ethanol (5 ml/mmol), a solution of the N-succinimide ester of the corresponding carboxylic acid (2 equivalents) in ethanol (5 ml/mmol) is added in drops, and 4 equivalents of sodium bicarbonate is added. Then, the reaction mixture is stirred at room temperature until the conversion is completed. For working-up, a phase separation is carried out between ethyl acetate/water, and the aqueous phase is extracted several times with ethyl acetate. The organic phase is dried with magnesium sulfate and concentrated by evaporation. The column-chromatographic purification is carried out on silica gel with a cyclohexane/ethyl acetate mixture as an eluant and yields the corresponding amides.

11β-{5-[Methyl(octanoyl)amino]pentyl}-8-vinyl-estra-1,3,5(10)-triene-3,17β-diol (38a)

In the reaction with octanoic acid-N-succinimidyl ester analogously to instructions 24.1, 9 mg of amine 31a yields 10 mg of amine 38a as colorless crystals [LC-MS: m/z theor.: 523, pract.: 524 $(M+H)^+$].

EXAMPLE 25

11β-(6-Chlorohexyl)-8-vinyl-estra-1,3,5(10)-triene-3,17β-diol (30b)

In the reaction analogously to instructions 1.2, 975 mg of steroid 13 yields 424 mg of 30b of a colorless foam, which, in addition to the chlorine compound (GC-MS: 81%, m/z theor.: 416, pract.: 416), contains the corresponding bromine compound (GC-MS: 17%, m/z theor.: 460, pract.: 460).

11β-[6-(Methylamino)hexyl]-8-vinylestra-1,3,5(10)-triene-3,17β-diol (31b)

In the reaction with methylamine (40% in water, 3 ml/mmol) with the addition of sodium carbonate analogously to instructions 17.2, 155 mg of product mixture 30b yields 152 mg of amine 31b as a colorless solid (GC-MS: m/z theor.: 411, pract.: 411).

EXAMPLE 26

11β-[6-(Dimethylamino)hexyl]-8-vinylestra-1,3,5(10)-triene-3,17β-diol (32b)

In the reaction with dimethylamine (2 M in tetrahydrofuran, 10 equivalents) with the addition of sodium carbonate analogously to instructions 17.2, 33 mg of mixture 30b yields 30 mg of amine 32b as a colorless foam (GC-MS: m/z theor.: 425, pract.: 425).

EXAMPLE 27

11β-[6-(Pyrrolidin-1-yl)hexyl]-8-vinylestra-1,3,5(10)-triene-3,17β-diol (33b)

In the reaction with pyrrolidine (10 equivalents) with the addition of sodium carbonate analogously to instructions 17.2, 32 mg of mixture 30b yields 33 mg of amine 33b as a colorless foam (GC-MS: m/z theor.: 451, pract.: 451).

EXAMPLE 28

11β-[6-(1-Piperidyl)hexyl]-8-vinylestra-1,3,5(10)-triene-3,17β-diol (34b)

In the reaction with piperidine (10 equivalents) with the addition of sodium carbonate analogously to instructions 17.2, 34 mg of mixture 30b yields 40 mg of amine 34b as a colorless foam (GC-MS: m/z theor.: 465, pract.: 465).

EXAMPLE 29

11β-(6-Morpholinohexyl)-8-vinylestra-1,3,5(10)-triene-3,17β-diol (35b)

In the reaction with morpholine (10 equivalents) with the addition of sodium carbonate analogously to instructions 17.2, 32 mg of mixture 30b yields 32 mg of amine 35b as a colorless foam (GC-MS: m/z theor.: 467, pract.: 467).

EXAMPLE 30

11β-{6-[Methyl(8,8,9,9,9-pentafluorononyl)amino]hexyl}-8-vinylestra-1,3,5(10)-triene-3,17β-diol (36b)

In the reaction with 8,8,9,9,9-pentafluorononyl tosylate analogously to instructions 22.1, 39 mg of amine 31b yields 22 mg of amine 36b as a colorless foam (GC-MS: m/z theor.: 627, pract.: 627).

EXAMPLE 31

11β-{6-[(7,7,8,8,9,9,9-Heptafluorononyl)methylamino]hexyl}-8-vinylestra-1,3,5(10)-triene-3,17β-diol (37b)

In the reaction with 7,7,8,8,9,9,9-heptafluorononyl tosylate analogously to instructions 22.1, 39 mg of amine 31b yields 21 mg of amine 37b as a colorless foam (GC-MS: m/z theor.: 663, pract.: 663).

EXAMPLE 32

11β-{6-[Methyl(octanoyl)amino]hexyl}-8-vinyl-estra-1,3,5(10)-triene-3,17β-diol (38b)

In the reaction with octanoic acid-N-succinimidyl ester analogously to instructions 24.1, 10 mg of amine 31b yields 10 mg of amine 38b as colorless crystals [LC-MS: m/z theor.: 537, pract.: 538 (M+H)$^+$].

EXAMPLE 33

General Instructions for Oxidation of Aldehydes 9a-b (Diagram 8)

A corresponding amount of aldehyde is dissolved in tert-butanol (5 ml/mmol). 2-Methylbut-2-ene (1 ml/mmol) as well as a solution that consists of sodium chlorite (1.1 equivalents) and sodium dihydrogen phosphate dihydrate (1.1 equivalents) in water (1 ml/mmol) are added in drops in succession. Then, the reaction mixture is stirred at room temperature until the conversion is completed. For working-up, a phase separation is carried out between diethyl ether/water, the aqueous phase is set at pH ~2 with 5% hydrochloric acid, saturated with sodium chloride and extracted several times with diethyl ether. The organic phase is washed with water and saturated sodium chloride solution, dried on magnesium sulfate and concentrated by evaporation. The column-chromatographic purification is carried out on silica gel with a cyclohexane/ethyl acetate mixture as an eluant and yields the corresponding carboxylic acids.

5-[17β-(tert-Butyldimethylsilyloxy)-3-methoxy-8-vinylestra-1,3,5(10)-trien-11β-yl]valeric acid (39a)

In the reaction analogously to instructions 33.1, 195 mg of aldehyde 9a yields 136 mg of carboxylic acid 39a as colorless crystals [LC-MS: m/z theor.: 526, pract.: 527 (M+H)$^+$].

General Operating Instructions for Converting Carboxylic Acids 39a-b into Amides 40a-b (Diagram 8)

A corresponding amount of carboxylic acid is dissolved in dichloromethane (10 ml/mmol) and cooled to −10° C. N-Methylmorpholine (4 equivalents), isobutyl chloroformate (4 equivalents) and, after another 30 minutes, nbutyl-methylamine (6 equivalents) are added in drops in succession. Then, the reaction mixture is stirred at room temperature until the conversion is completed. For working-up, a phase separation between dichloromethane/saturated sodium bicarbonate solution is carried out. The aqueous phase is extracted several times with dichloromethane, the combined organic phases are washed with saturated sodium chloride solution, dried on magnesium sulfate and concentrated by evaporation. The column-chromatographic purification is carried out on silica gel with a cyclohexane/ethyl acetate mixture as an eluant and yields the corresponding amides.

N-nButyl-N-methyl-5-[17β-(tert-butyldimethylsilyloxy)-3-methoxy-8-vinylestra-1,3,5(10)-trien-11β-yl]valeramide (40a)

In the reaction analogously to instructions 33.2, 130 mg of carboxylic acid 39a yields 81 mg of amide 40a as a colorless foam [LC-MS: m/z theor.: 595, pract.: 596 (M+H)$^+$].

N-nButyl-N-methyl-5-[3,17β-dihydroxy-8-vinylestra-1,3,5(10)-trien-11β-yl]valeramide (41a)

In the reaction analogously to instructions 1.2, 80 mg of amide 40a yields 31 mg of estratrienediol 41a as a colorless foam [LC-MS: m/z theor.: 467, pract.: 468 (M+H)$^+$].

EXAMPLE 34

6-[17β-(tert-Butyldimethylsilyloxy)-3-methoxy-8-vinylestra-1,3,5(10)-trien-11β-yl]caproic acid (39b)

In the reaction analogously to instructions 33.1, 150 mg of aldehyde 9b yields 108 mg of carboxylic acid 39b as colorless crystals [LC-MS: m/z theor.: 540, pract.: 541 (M+H)$^+$].

N-nButyl-N-methyl-6-[17β-(tert-butyldimethylsilyloxy)-3-methoxy-8-vinylestra-1,3,5(10)-trien-11β-yl]capronamide (40b)

In the reaction analogously to instructions 33.2, 105 mg of carboxylic acid 39b yields 63 mg of amide 40b as a colorless foam [LC-MS: m/z theor.: 609, pract.: 610 (M+H)$^+$].

N-nButyl-N-methyl-6-[3,17β-dihydroxy-8-vi-
nylestra-1,3,5(10)-trien-11β-yl]capronamide (41b)

In the reaction analogously to instructions 1.2, 60 mg of amide 40b yields 28 mg of estratrienediol 41b as a colorless foam [LC-MS: m/z theor.: 481, pract.: 482 (M+H)$^+$].

EXAMPLE 35

11β-(5-Thiocyanatopentyl)-8-vinylestra-1,3,5(10)-trien-3,17β-diol (42) (Diagram 7)

8.4 mg of potassium rhodanide and 32 mg of tetrabutylammonium iodide are added in succession to a solution of 13 mg of bromide 30a in 0.3 ml of N,N-dimethylformamide, and the reaction solution is then stirred until the reaction is completed. For working-up, a phase separation is carried out by means of ethyl acetate/water, and the aqueous phase is extracted several times with ethyl acetate. The organic phase is washed with water and saturated sodium chloride solution, dried on magnesium sulfate, and concentrated by evaporation. The residue is purified by column chromatography (cyclohexane/ethyl acetate), and yields 9 mg of rhodanide 42 as a colorless foam [LC-MS: m/z theor.: 425, pract.: 426 (M+H)$^+$].

EXAMPLE 36

6-[3,17β-Dihydroxy-8-vinylestra-1,3,5(10)-trien-11β-yl]capronitrile (43a) (Diagram 2)

In the reaction analogously to instructions 1.2, 16 mg of steroid 11a yields 7 mg of estratrienediol 43a as a colorless foam (GC-MS: m/z theor.: 393, pract.: 393).

EXAMPLE 37

7-[3,17β-Dihydroxy-8-vinylestra-1,3,5(10)-trien-11β-yl]heptanitrile (43b)

In the reaction analogously to instructions 1.2, 22 mg of steroid 11b yields 12 mg of estratrienediol 43b as a colorless foam (GC-MS: m/z theor.: 407, pract.: 407).

EXAMPLE 38

General Operating Instructions for Oppenauer-Oxidation of the 17β-Hydroxy Group

Cyclohexanone (50 equivalents) and aluminum isopropylate (10 equivalents) are added in succession to a solution of the corresponding alcohol (1 equivalent) in toluene (20 ml/mmol). The reaction solution is then refluxed until the reaction is completed. For working-up, the reaction solution is acidified at room temperature with 1N hydrochloric acid, and the phases are separated by means of diethyl ether/water. The organic phase is washed with water and saturated sodium chloride solution, dried on magnesium sulfate, the diethyl ether and the toluene are removed in a vacuum rotary evaporator, and the residual amount of solvent is azeotropically distilled off with water. The thus obtained residue is purified by column chromatography (cyclohexane/ethyl acetate), and the corresponding 17-ketones are obtained.

3-Hydroxy-11β-[(R)-6,6,6-Trifluoro-5-hydroxyhexyl]-8-vinyl-estra-1,3,5(10)-trien-17-one (44a D1)

In the reaction analogously to instructions 38.1, 50 mg of alcohol 15a D1 yields 40 mg of ketone 44a D1 as a colorless foam (GC-MS: m/z theor.: 450, pract.: 450).

17α-Methyl-11-[(R)-6,6,6-Trifluoro-5-hydroxyhexyl]-8-vinyl-estra-1,3,5(10)-triene-3,17β-diol (45a D1)

In the reaction analogously to instructions 13.1, 39 mg of ketone 44a D1 yields 30 mg of alcohol 45a D1 as a colorless foam (GC-MS: m/z theor.: 466, pract.: 466).

EXAMPLE 39

3-Hydroxy-11β-[(S)-6,6,6-Trifluoro-5-hydroxyhexyl]-8-vinyl-estra-1,3,5(10)-trien-17-one (44a D2)

In the reaction analogously to instructions 38.1, 50 mg of alcohol 15a D2 yields 42 mg of ketone 44a D2 as a colorless foam (GC-MS: m/z theor.: 450, pract.: 450).

17α-Methyl-11β-[(S)-6,6,6-Trifluoro-5-hydroxyhexyl]-8-vinyl-estra-1,3,5(10)-triene-3,17β-diol (45a D2)

In the reaction analogously to instructions 13.1, 28 mg of ketone 44a D2 yields 19 mg of alcohol 45a D2 as a colorless foam (GC-MS: m/z/theor.: 466, pract.: 466).

EXAMPLE 40

3-Hydroxy-11β-(7,7,7-Trifluoro-6-hydroxyheptyl)-8-vinyl-estra-1,3,5(10)-trien-17-one (44b D1)

In the reaction analogously to instructions 38.1, 35 mg of alcohol 15d D1 yields 27 mg of ketone 44b D1 as a colorless foam (GC-MS: m/z theor.: 464, pract.: 464).

17α-Methyl-11β-(7,7,7-Trifluoro-6-hydroxyheptyl)-8-vinyl-estra-1,3,5(10)-triene-3,17β-diol (45b D1)

In the reaction analogously to instructions 13.1, 25 mg of ketone 44b D1 yields mg of alcohol 45b D1 as a colorless foam (GC-MS: m/z theor.: 480, pract.: 480).

EXAMPLE 41

3-Hydroxy-11β-(7,7,7-trifluoro-6-hydroxyheptyl)-8-vinyl-estra-1,3,5(10)-trien-17-one (44b D2)

In the reaction analogously to instructions 38.1, 35 mg of alcohol 15b D2 yields mg of ketone 44b D2 as a colorless foam (GC-MS: m/z theor.: 464, pract.: 464).

17α-Methyl-11β-(7,7,7-trifluoro-6-hydroxyheptyl)-8-vinyl-estra-1,3,5(10)-triene-3,17β-diol (45b D2)

In the reaction analogously to instructions 13.1, 23 mg of ketone 44b D2 yields 18 mg of alcohol 45b D2 as a colorless foam (GC-MS: m/z theor.: 480, pract.: 480).

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius, and all parts and percentages are by weight, unless otherwise indicated.

The entire disclosures of all applications, patents and publications, cited herein and of corresponding German Application No. 10318896.7, filed Apr. 22, 2003, and U.S. Provisional Application Ser. No. 60/464,630, filed Apr. 23, 2003, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and, without departing from the spirit and scope thereof, can make various changes and modifications of the invention to adapt it to various usages and conditions.

The invention claimed is:

1. A compound of formula I

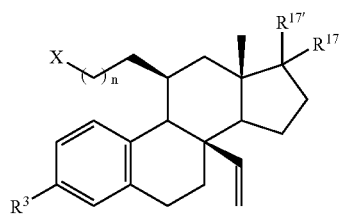

in which
R$^3$ represents a group R$^{19}$—O—, R$^{20}$SO$_2$—O—, or —O—C(O)R$^{21}$;
n represents 3, 4, or 5:
X represents a group of formula II

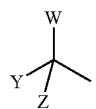

in which
Z and W, independently of one another, represent R$^{19}$,
or
Z and W together represent an oxygen atom,
Y represents OR$^{19}$, —CN, —SCN, a halogen atom, R$^{20}$, R$^{20}$SO$_2$—O—;
or
Y represents R$^{19}$ or R$^{20}$, if Z and W together represent an oxygen atom;
R$^{17}$ and R$^{17'}$ together represent an oxygen atom, or a group =CR$^{23}$R$^{24}$,
in which
R$^{23}$ and R$^{24}$, independently of one another, represent a hydrogen atom or a halogen;
or
R$^{17}$ represents hydrogen, —OR$^{19}$ or halogen;
R$^{17'}$ represents R$^{19}$, —OR$^{19}$, halogen, R$^{20}$SO$_2$—O—, —C(O)R$^{21}$ or —O—C(O)R$^{21}$;

R$^{19}$ represents a hydrogen atom,
a radical of formula C$_p$F$_q$H$_r$ with p=1, 2, 3, 4, 5, 6, 7, 8, 9; q>1 and q+r=2p+1;
an unbranched C$_1$-C$_8$-alkyl group or branched C$_3$-C$_6$-alkyl group, a C$_3$-C$_6$-cycloalkyl group that is optionally substituted with a phenyl radical, a (C$_3$-C$_6$-cycloalkyl)-C$_1$-C$_4$-alkylene group, a branched or unbranched C$_2$-C$_5$-alkenyl group, a C$_2$-C$_5$-alkinyl group; or an unsubstituted or substituted aryl-, heteroaryl-, heterocyclyl-, aryl-C$_1$-C$_4$-alkylene-, or heteroaryl-C$_1$-C$_4$-alkylene group;
R$^{20}$ represents an R$^{21}$R$^{22}$N— group, a group —C(NOR$^{19}$)H, or a group of formula III

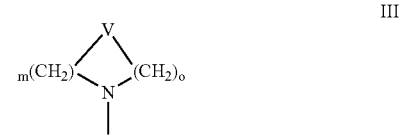

in which
V represents —CH$_2$—, an oxygen atom or a sulfur atom, or —N(R$^{25}$)—;
m represents 0, 1, 2, 3, 4, 5, 6, 7 or 8;
o represents 0, 1, 2, 3, 4, 5, 6, 7 or 8,
whereby their sum
m+o is 2, 3, 4, 5, 6, 7, 8, 9, 10, 11, 12;
R$^{21}$ and R$^{22}$, independently of one another, represent R$^{19}$;
R$^{25}$ represents R$^{19}$, R$^{20}$SO$_2$— or an acyl group —C(O)R$^{21}$.

2. A compound according to claim 1, wherein Y≡OH, —CN, —SCN, a halogen, or R$^{20}$.

3. A compound according to claim 1, wherein Y=R$^{20}$, and Z and W together represent an oxygen atom.

4. A compound according to claim 1, wherein
Y represents —OH, —CN, —SCN, a halogen atom, or R$^{20}$;
and
R$^{17}$ and R$^{17'}$ together represent an oxygen atom,
or
R$^{17}$ represents hydrogen, or —OH;
R$^{17'}$ represents hydrogen, —OH, C$_1$-C$_4$-alkyl group, C$_2$-C$_5$-alkenyl group,
a C$_2$-C$_5$-alkinyl group, or a trifluoromethyl group.

5. A compound according to claim 1, wherein
Y represents R$^{20}$, and Z and W together represent an oxygen atom,
and
R$^{17}$ and R$^{17'}$ together represent an oxygen atom,
or
R$^{17}$ represents hydrogen, or —OH;
R$^{17'}$ represents hydrogen, —OH, C$_1$-C$_4$-alkyl group, C$_2$-C$_5$-alkenyl group,
a C$_2$-C$_5$-alkinyl group, or a trifluoromethyl group.

6. A compound according to claim 1, which is
11β-[(R)6,6,6-Trifluoro-5-hydroxyhexyl]-8-vinyl-estra-1,3,5(10)-triene-3,17β-diol,
11β-[(S)6,6,6-Trifluoro-5-hydroxyhexyl]-8-vinyl-estra-1,3,5(10)-triene-3,17β-diol,
11β-[(R)7,7,7-Trifluoro-6-hydroxyheptyl]-8-vinyl-estra-1,3,5(10)-triene-3,17β-diol,
11β-[(S)7,7,7-Trifluoro-6-hydroxyheptyl]-8-vinyl-estra-1,3,5(10)-triene-3,17β-diol,
11β-[(R)8,8,8-Trifluoro-7-hydroxyoctyl]-8-vinyl-estra-1,3,5(10)-triene-3,17β-diol, 11β-[(S)8,8,8-Trifluoro-7-hydroxyoctyl]-8-vinyl-estra-1,3,5(10)-triene-3,17β-diol,
11β-[6,6,6-Trifluoro-5-hydroxy-5-(trifluoromethyl)hexyl]-8-vinyl-estra-1,3,5(10)-triene-3,17β-diol,
11β-[7,7,7-Trifluoro-6-hydroxy-6-(trifluoromethyl)heptyl]-8-vinyl-estra-1,3,5(10)-triene-3,17β-diol,
11β-[8,8,8-Trifluoro-7-hydroxy-7-(trifluoromethyl)octyl]-8-vinyl-estra-1,3,5(10)-triene-3,17β-diol,
11β-[(R)7,7,7,6,6-Pentafluoro-5-hydroxyheptyl]-8-vinyl-estra-1,3,5(10)-triene-3,17β-diol,
11β-[(S)7,7,7,6,6-Pentafluoro-5-hydroxyheptyl]-8-vinyl-estra-1,3,5(10)-triene-3,17β-diol,
11β-[(R)8,8,8,7,7-Pentafluoro-6-hydroxyoctyl]-8-vinyl-estra-1,3,5(10)-triene-3,17β-diol,
11β-[(S)8,8,8,7,7-Pentafluoro-6-hydroxyoctyl]-8-vinyl-estra-1,3,5(10)-triene-3,17β-diol,
11β-[(R)9,9,9,8,8-Pentafluoro-7-hydroxynonyl]-8-vinyl-estra-1,3,5(10)-triene-3,17β-diol,
11β-[(S)9,9,9,8,8-Pentafluoro-7-hydroxynonyl]-8-vinyl-estra-1,3,5(10)-triene-3,17β-diol,
11β-[(R)8,8,8,7,7,6,6-Heptafluoro-5-hydroxyoctyl]-8-vinyl-estra-1,3,5(10)-triene-3,17β-diol,
11β-[(S)8,8,8,7,7,6,6-Heptafluoro-5-hydroxyoctyl]-8-vinyl-estra-1,3,5(10)-triene-3,17β-diol,
11β-[(R)9,9,9,8,8,7,7-Heptafluoro-6-hydroxynonyl]-8-vinyl-estra-1,3,5(10)-triene-3,17β-diol,
11β-[(S)9,9,9,8,8,7,7-Heptafluoro-6-hydroxynonyl]-8-vinyl-estra-1,3,5(10)-triene-3,17β-diol,
11β-[(R)10,10,10,9,9,8,8-Heptafluoro-7-hydroxydecyl]-8-vinyl-estra-1,3,5(10)-triene-3,17β-diol,
11β-[(S)10,10,10,9,9,8,8-Heptafluoro-7-hydroxydecyl]-8-vinyl-estra-1,3,5(10)-triene-3,17β-diol,
11β-(5-Bromopentyl)-8-vinyl-estra-1,3,5(10)-triene-3,17β-diol,
11β-[5-(Methylamino)pentyl]-8-vinylestra-1,3,5(10)-triene-3,17β-diol,
11β-[5-(Dimethylamino)pentyl]-8-vinylestra-1,3,5(10)-triene-3,17β-diol,
11β-[5-(Pyrrolidin-1-yl)pentyl]-8-vinylestra-1,3,5(10)-triene-3,17β-diol,
11β-[5-(1-Piperidyl)pentyl]-8-vinylestra-1,3,5(10)-triene-3,17β-diol,
11β-(5-Morpholinopentyl)-8-vinylestra-1,3,5(10)-triene-3,17β-diol,
11β-{5-[Methyl(9,9,9,8,8-pentafluorononyl)amino]pentyl}-8-vinylestra-1,3,5(10)-triene-3,17β-diol,
11β-{5-[(9,9,9,8,8,7,7-Heptafluorononyl)methylamino]pentyl}-8-vinylestra-1,3,5(10)-triene-3,17β-diol,
11β-{5-[Methyl(octanoyl)amino]pentyl}-8-vinyl-estra-1,3,5(10)-triene-3,17β-diol,
11β-(6-Chlorohexyl)-8-vinyl-estra-1,3,5(10)-triene-3,17β-diol,
11β-[6-(Methylamino)hexyl]-8-vinylestra-1,3,5(10)-triene-3,17β-diol,
11β-[6-(Dimethylamino)hexyl]-8-vinylestra-1,3,5(10)-triene-3,17β-diol, 11β-[6-(Pyrrolidin-1-yl)hexyl]-8-vinylestra-1,3,5(10)-triene-3,17β-diol,
11β-[6-(1-Piperidyl)hexyl]-8-vinylestra-1,3,5(10)-triene-3,17β-diol,
11β-(6-Morpholinohexyl)-8-vinylestra-1,3,5(10)-triene-3,17β-diol,
11β-{6-[Methyl(9,9,9,8,8-pentafluorononyl)amino]hexyl}-8-vinylestra-1,3,5(10)-triene-3,17β-diol,
11β-{6-[(9,9,9,8,8,7,7-Heptafluorononyl)methylamino]hexyl}-8-vinylestra-1,3,5(10)-triene-3,17β-diol,
11β-{6-[Methyl(octanoyl)amino]hexyl}-8-vinyl-estra-1,3,5(10)-triene-3,17β-diol,
11β-(7-Bromoheptyl)-8-vinyl-estra-1,3,5(10)-triene-3,17β-diol,
11β-[7-(Methylamino)heptyl]-8-vinylestra-1,3,5(10)-triene-3,17β-diol,
11β-[7-(Dimethylamino)heptyl]-8-vinylestra-1,3,5(10)-triene-3,17β-diol,
11β-[7-(Pyrrolidin-1-yl)heptyl]-8-vinylestra-1,3,5(10)-triene-3,17β-diol,
11β-[7-(1-Piperidyl)heptyl]-8-vinylestra-1,3,5(10)-triene-3,17β-diol,
11β-(7-Morpholinoheptyl)-8-vinylestra-1,3,5(10)-triene-3,17β-diol,
11β-{7-[Methyl(9,9,9,8,8-pentafluorononyl)amino]heptyl}-8-vinylestra-1,3,5(10)-triene-3,17β-diol,
11β-{7-[(9,9,9,8,8,7,7-Heptafluorononyl)methylamino]heptyl}-8-vinylestra-1,3,5(10)-triene-3,17β-diol,
11β-{7-[Methyl(octanoyl)amino]heptyl}-8-vinyl-estra-1,3,5(10)-triene-3,17β-diol,
N-nButyl-N-methyl-5-[3,17β-dihydroxy-8-vinylestra-1,3,5(10)-trien-11β-yl]valeramide,
N-nButyl-N-methyl-6-[3,17β-dihydroxy-8-vinylestra-1,3,5(10)-trien-11β-yl]capronamide,
N-nButyl-N-methyl-7-[3,17β-dihydroxy-8-vinylestra-1,3,5(10)-trien-11β-yl]enanthoamide,
11β-(5-Thiocyanatopentyl)-8-vinylestra-1,3,5(10)-triene-3,17β-diol,
11β-(6-Thiocyanatohexyl)-8-vinylestra-1,3,5(10)-triene-3,17β-diol,
11β-(7-Thiocyanatoheptyl)-8-vinylestra-1,3,5(10)-triene-3,17β-diol,
6-[3,17β-Dihydroxy-8-vinylestra-1,3,5(10)-trien-11β-yl]capronitrile,
7-[3,17β-Dihydroxy-8-vinylestra-1,3,5(10)-trien-11β-yl]enanthonitrile,
17β-Hydroxy-11β-[(R)6,6,6-trifluoro-5-hydroxyhexyl]-8-vinyl-estra-1,3,5(10)-trien-3-yl-sulfamate,
17β-Hydroxy-11β-[(S)6,6,6-trifluoro-5-hydroxyhexyl]-8-vinyl-estra-1,3,5(10)-trien-3-yl-sulfamate,
17β-Hydroxy-11β-[(R)7,7,7-trifluoro-6-hydroxyheptyl]-8-vinyl-estra-1,3,5(10)-trien-3-yl-sulfamate,
17β-Hydroxy-11β-[(S)7,7,7-trifluoro-6-hydroxyheptyl]-8-vinyl-estra-1,3,5(10)-trien-3-yl-sulfamate,
17β-Hydroxy-11β-[(R)8,8,8-trifluoro-7-hydroxyoctyl]-8-vinyl-estra-1,3,5(10)-trien-3-yl-sulfamate,
17β-Hydroxy-11β-[(S)8,8,8-trifluoro-7-hydroxyoctyl]-8-vinyl-estra-1,3,5(10)-trien-3-yl-sulfamate,
17β-Hydroxy-11β-[6,6,6-trifluoro-5-hydroxy-5-(trifluoromethyl)hexyl]-8-vinyl-estra-1,3,5(10)-trien-3-yl-sulfamate,
17β-Hydroxy-11β-[7,7,7-trifluoro-6-hydroxy-6-(trifluoromethyl)heptyl]-8-vinyl-estra-1,3,5(10)-trien-3-yl-sulfamate,
17β-Hydroxy-11β-[8,8,8-trifluoro-7-hydroxy-7-(trifluoromethyl)octyl]-8-vinyl-estra-1,3,5(10)-trien-3-yl-sulfamate,
17β-Hydroxy-11β-[(R)7,7,7,6,6-pentafluoro-5-hydroxyheptyl]-8-vinyl-estra-1,3,5(10)-trien-3-yl-sulfamate,
17β-Hydroxy-11β-[(S)7,7,7,6,6-pentafluoro-5-hydroxyheptyl]-8-vinyl-estra-1,3,5(10)-trien-3-yl-sulfamate,
17β-Hydroxy-11β-[(R)8,8,8,7,7-pentafluoro-6-hydroxyoctyl]-8-vinyl-estra-1,3,5(10)-trien-3-yl-sulfamate,
17β-Hydroxy-11β-[(S)8,8,8,7,7-pentafluoro-6-hydroxyoctyl]-8-vinyl-estra-1,3,5(10)-trien-3-yl-sulfamate,
17β-Hydroxy-11β-[(R)9,9,9,8,8-pentafluoro-7-hydroxynonyl]-8-vinyl-estra-1,3,5(10)-trien-3-yl-sulfamate,
17β-Hydroxy-11β-[(S)9,9,9,8,8-pentafluoro-7-hydroxynonyl]-8-vinyl-estra-1,3,5(10)-trien-3-yl-sulfamate, 11β-[5-(Dimethylamino)pentyl]-17β-hydroxy-8-vinylestra-1,3,5(10)-trien-3-yl-sulfamate,
17β-Hydroxy-11β-[5-(pyrrolidin-1-yl)pentyl]-8-vinylestra-1,3,5(10)-trien-3-yl-sulfamate,
17β-Hydroxy-11β-[5-(1-piperidyl)pentyl]-8-vinylestra-1,3,5(10)-trien-3-yl-sulfamate,
17β-Hydroxy-11β-(5-morpholinopentyl)-8-vinylestra-1,3,5(10)-trien-3-yl-sulfamate,
11β-[6-(Dimethylamino)hexyl]-17β-hydroxy-8-vinylestra-1,3,5(10)-trien-3-yl-sulfamate,
17β-Hydroxy-11β-[6-(pyrrolidin-1-yl)hexyl]-8-vinylestra-1,3,5(10)-trien-3-yl-sulfamate,
17β-Hydroxy-11β-[6-(1-piperidyl)hexyl]-8-vinylestra-1,3,5(10)-trien-3-yl-sulfamate,
17β-Hydroxy-11β-(6-morpholinohexyl)-8-vinylestra-1,3,5(10)-trien-3-yl-sulfamate,
11β-[7-(Dimethylamino)heptyl]-17β-hydroxy-8-vinylestra-1,3,5(10)-trien-3-yl-sulfamate,
17β-Hydroxy-11β-[7-(pyrrolidin-1-yl)heptyl]-8-vinylestra-1,3,5(10)-trien-3-yl-sulfamate,
17β-Hydroxy-11β-[7-(1-piperidyl)heptyl]-8-vinylestra-1,3,5(10)-trien-3-yl-sulfamate,
17β-Hydroxy-11β-(7-morpholinoheptyl)-8-vinylestra-1,3,5(10)-trien-3-yl-sulfamate,
11β-[(R)7,7,6-Trifluoro-6-hydroxyhept-7-enyl]-8-vinyl-estra-1,3,5(10)-triene-3,17β-diol,
11β-[(S)7,7,6-Trifluoro-5-hydroxyhept-6-enyl]-8-vinyl-estra-1,3,5(10)-triene-3, 17β-diol,
11β-[(R)8,8,7-Trifluoro-6-hydroxyoct-7-enyl]-8-vinyl-estra-1,3,5(10)-triene-3,17β-diol,
11β-[(S)8,8,7-Trifluoro-6-hydroxyoct-7-enyl]-8-vinyl-estra-1,3,5(10)-triene-3,17β-diol,
11β-[(R)9,9,8-Trifluoro-7-hydroxynon-8-enyl]-8-vinyl-estra-1,3,5(10)-triene-3,17β-diol,
11β-[(S)9,9,8-Trifluoro-7-hydroxynon-3-enyl]-8-vinyl-estra-1,3,5(10)-triene-3,17β-diol,
(R)11β-[5-Hydroxyhexyl]-8-vinyl-estra-1,3,5(10)-triene-3,17β-diol,
(S)11β-[5-Hydroxyhexyl]-8-vinyl-estra-1,3,5(10)-triene-3,17β-diol,
(R)11β-[6-Hydroxyheptyl]-8-vinyl-estra-1,3,5(10)-triene-3,17β-diol,
(S)11β-[6-Hydroxyheptyl]-8-vinyl-estra-1,3,5(10)-triene-3,17β-diol,
(R)11β-[7-Hydroxyoctyl]-8-vinyl-estra-1,3,5(10)-triene-3,17β-diol,
(S)11β-[7-Hydroxyoctyl]-8-vinyl-estra-1,3,5(10)-triene-3,17β-diol,
11β-[5-Methyl-5-hydroxyhexyl]-8-vinyl-estra-1,3,5(10)-triene-3,17β-diol,
11β-[6-Methyl-6-hydroxyheptyl]-8-vinyl-estra-1,3,5(10)-triene-3,17β-diol,
11β-[7-Methyl-7-hydroxyoctyl]-8-vinyl-estra-1,3,5(10)-triene-3,17β-diol,
17α-Methyl-11β-[(R)6,6,6-trifluoro-5-hydroxyhexyl]-8-vinyl-estra-1,3,5(10)-triene-3,17β-diol,
17α-Methyl-11β-[(S)6,6,6-trifluoro-5-hydroxyhexyl]-8-vinyl-estra-1,3,5(10)-triene-3,17β-diol,
17α-Methyl-11β-[(R)7,7,7-trifluoro-6-hydroxyheptyl]-8-vinyl-estra-1,3,5(10)-triene-3,17β-diol,
17α-Methyl-11β-[(S)7,7,7-trifluoro-6-hydroxyheptyl]-8-vinyl-estra-1,3,5(10)-triene-3,17β-diol,
17α-Methyl-11β-[(R)8,8,8-Trifluoro-7-hydroxyoctyl]-8-vinyl-estra-1,3,5(10)-triene-3,17β-diol,
17α-Methyl-11β-[(S)8,8,8-trifluoro-7-hydroxyoctyl]-8-vinyl-estra-1,3,5(10)-triene-3,17β-diol),
17β-Hydroxy-11β-[(R)8,8,8,7,7,6,6-heptafluoro-5-hydroxyoctyl]-8-vinyl-estra-1,3,5(10)-trien-3-yl-sulfamate,
17β-Hydroxy-11β-[(S)8,8,8,7,7,6,6-heptafluoro-5-hydroxyoctyl]-8-vinyl-estra-1,3,5(10)-trien-3-yl-sulfamate,
17β-Hydroxy-11β-[(R)9,9,9,8,8,7,7-heptafluoro-6-hydroxynonyl]-8-vinyl-estra-1,3,5(10)-trien-3-yl-sulfamate,
17β-Hydroxy-11β-[(S)9,9,9,8,8,7,7-heptafluoro-6-hydroxynonyl]-8-vinyl-estra-1,3,5(10)-trien-3-yl-sulfamate,
17β-Hydroxy-11β-[(R)10,10,10,9,9,8,8-heptafluoro-7-hydroxydecyl]-8-vinyl-estra-1,3,5(10)-trien-3-yl-sulfamate,
17β-Hydroxy-11β-[(S)10,10,10,9,9,8,8-heptafluoro-7-hydroxydecyl]-8-vinyl-estra-1,3,5(10)-trien-3-yl-sulfamate,
17β-Hydroxy-11β-[(R)7,7,6-trifluoro-5-hydroxyhept-6-enyl]-8-vinyl-estra-1,3,5(10)-trien-3-yl-sulfamate,
17β-Hydroxy-11β-[(S)7,7,6-trifluoro-5-hydroxyhept-6-enyl]-8-vinyl-estra-1,3,5(10)-trien-3-yl-sulfamate,
17β-Hydroxy-11β-[(R)8,8,7-trifluoro-6-hydroxyoct-7-enyl]-8-vinyl-estra-1,3,5(10)-trien-3-yl-sulfamate,
17β-Hydroxy-11β-[(S)8,8,7-trifluoro-6-hydroxyoct-7-enyl]-8-vinyl-estra-1,3,5(10)-trien-3-yl-sulfamate,
17β-Hydroxy-11β-[(R)9,9,8-trifluoro-7-hydroxynon-8-enyl]-8-vinyl-estra-1,3,5(10)-trien-3-yl-sulfamate,
17β-Hydroxy-11β-[(S)9,9,8-trifluoro-7-hydroxynon-8-enyl]-8-vinyl-estra-1,3,5(10)-trien-3-yl-sulfamate,
17β-Hydroxy-17α-methyl-11β-[(1R)6,6,6-trifluoro-5-hydroxyhexyl]-8-vinyl-estra-1,3,5(10)-trien-3-yl-sulfamate,
17β-Hydroxy-17α-methyl-11β-[(S)6,6,6-trifluoro-5-hydroxyhexyl]-8-vinyl-estra-1,3,5(10)-trien-3-yl-sulfamate,
17β-Hydroxy-17α-methyl-11β-[(R)7,7,7-trifluoro-6-hydroxyheptyl]-8-vinyl-estra-1,3,5(10)-trien-3-yl-sulfamate,
17β-Hydroxy-17α-methyl-11β-[(S)7,7,7-trifluoro-6-hydroxyheptyl]-8-vinyl-estra-1,3,5(10)-trien-3-yl-sulfamate,
17β-Hydroxy-17α-methyl-11β-[(R)8,8,8-trifluoro-7-hydroxyoctyl]-8-vinyl-estra-1,3,5(10)-trien-3-yl-sulfamate
or
17β-Hydroxy-17α-methyl-11β-[(S)8,8,8-trifluoro-7-hydroxyoctyl]-8-vinyl-estra-1,3,5(10)-trien-3-yl-sulfamate.

7. A pharmaceutical composition comprising at least one compound according to claim 1 as well as a pharmaceutically compatible adjuvant and/or vehicle.

8. A pharmaceutical composition comprising a compound according to claim 1 and at least one compound that is a GnRH antagonist, a progesterone receptor antagonist, a mesoprogestin, a gestagen or a tissue-selective gestagen.

9. A method of preparing a pharmaceutical agent comprising admixing a compound according to claim 1 with a pharmaceutically compatible adjuvant and/or vehicle.

10. A method for contraception in women comprising administering to a patient in need thereof a pharmaceutically effective amount of a compound according to claim 1.

11. A method for contraception in men comprising administering to a patient in need thereof a pharmaceutically effective amount of a compound according to claim 1.

12. A method for treating benign or malignant proliferative diseases of the ovary comprising administering to a patient in need thereof a pharmaceutically effective amount of a compound according to claim 1.

13. A method according to claim 12, wherein said disease is ovarian cancer.

14. A method according to claim 12, for treating a granulosa cell tumor.

15. A method according to claim 12, wherein the function of other estrogen-sensitive organs are not impaired.

16. An intermediate product of formula VI in which
R$^3$ represents a group R$^{19}$—O—, R$^{20}$SO$_2$—O—, or —O—C(O)R$^{21}$;
n represents 3, 4, or 5:
X represents a group of formula II in which
Z and W, independently of one another, represent R$^{19}$,
or
Z and W together represent an oxygen atom,
Y represents OR$^{19}$, —CN, —SCN, a halogen atom, R$^{20}$, R$^{20}$SO$_2$—O—;
or
Y represents R$^{19}$ or R$^{20}$, if Z and W together represent an oxygen atom;
R$^{17}$ and R$^{17'}$ together represent an oxygen atom, or a group =CR$^{23}$R$^{24}$,
in which
R$^{23}$ and R$^{24}$, independently of one another, represent a hydrogen atom or a halogen;
or
R$^{17}$ represents hydrogen, —OR$^{19}$ or halogen;
R$^{17'}$ represents R$^{19}$, —OR$^{19}$, halogen, R$^{20}$SO$_2$—O—, —C(O)R$^{21}$ or —O—C(O)R$^{21}$;
R$^{19}$ represents a hydrogen atom,
a radical of formula C$_p$F$_q$H$_r$ with p=1, 2, 3, 4, 5, 6, 7, 8, 9; q>1 and q+r=2p+1;
an unbranched C$_1$-C$_8$-alkyl group or branched C$_3$-C$_6$-alkyl group, a C$_3$-C$_6$-cycloalkyl group that is optionally substituted with a phenyl radical, a (C$_1$-C$_6$-cycloalkyl)-C$_1$-C$_4$-alkylene group, a branched or unbranched C$_2$-C$_5$-alkenyl group, a C$_2$-C$_5$-alkinyl group, or an unsubstituted or substituted aryl-, heteroaryl-, heterocyclyl-, aryl-C$_1$-C$_4$-alkylene-, or heteroaryl-C$_1$-C$_4$-alkylene group;
R$^{20}$ represents an R$^{21}$R$^{22}$N— group, a group —C(NOR$^{19}$)H, or a group of formula III in which
V represents —CH$_2$—, an oxygen atom or a sulfur atom, or —N(R$^{25}$)—;
m represents 0, 1, 2, 3, 4, 5, 6, 7 or 8,
o represents 0.1, 2, 3, 4, 5, 6, 7 or 8,
whereby their sum
m+o is 2, 3, 4, 5, 6, 7, 8, 9, 10, 11, 12;
R$^{21}$ and R$^{22}$, independently of one another, represent R$^{19}$;
R$^{25}$ represents R$^{19}$, R$^{20}$SO$_2$— or an acyl group —C(O)R$^{21}$.

17. A compound of formula VII in which
R$^3$ represents a group R$^{19}$—O—, R$^{20}$SO$_2$—O—, or —O—C(O)R$^{21}$;
n represents 3, 4, or 5:
X represents a group of formula II in which
Z and W, independently of one another, represent R$^{19}$,
or
Z and W together represent an oxygen atom,
Y represents OR$^{19}$, —CN, —SCN, a halogen atom, R$^{20}$, R$^{20}$SO$_2$—O—;
or
Y represents R$^{19}$ or R$^{20}$, if Z and W together represent an oxygen atom;
R$^{17}$ and R$^{17'}$ together represent an oxygen atom, or a group =CR$^{23}$R$^{24}$,
in which
R$^{23}$ and R$^{24}$, independently of one another, represent a hydrogen atom or a halogen;
or
R$^{17}$ represents hydrogen, —OR$^{19}$ or halogen;
R$^{17'}$ represents R$^{19}$, —OR$^{19}$, halogen, R$^{20}$SO$_2$—O—, —C(O)R$^{21}$ or —O—C(O)R$^{21}$;
R$^{19}$ represents a hydrogen atom,
a radical of formula C$_p$F$_q$H$_r$ with p=1, 2, 3, 4, 5, 6, 7, 8, 9: q>1 and q+r=2p+1,
an unbranched C$_1$-C$_8$-alkyl group or branched C$_3$-C$_6$-alkyl group, a C$_3$-C$_6$-cycloalkyl group that is optionally substituted with a phenyl radical, a (C$_3$-C$_6$-cycloalkyl)-C$_1$-C$_4$-alkylene group, a branched or unbranched C$_2$-C$_5$-alkenyl group, a C$_2$-C$_5$-alkinyl group; or an unsubstituted or substituted aryl-, heteroaryl-, heterocyclyl-, aryl-C$_1$-C$_4$-alkylene-, or heteroaryl-C$_1$-C$_4$-alkylene group;

$R^{20}$ represents an $R^{21}R^{22}N$— group, a group —$C(NOR^{19})$H, or a group of formula III

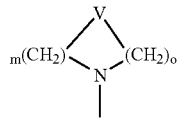

in which
V represents —$CH_2$—, an oxygen atom or a sulfur atom, or =N—$R^{25}$;
m represents 0.1, 2, 3, 4, 5, 6, 7 or 8;
o represents 0, 1, 2, 3, 4, 5, 6, 7 or 8,
whereby their sum
m+o is 2, 3, 4, 5, 6, 7, 8, 9, 10, 11, 12;
$R^{21}$ and $R^{22}$, independently of one another, represent $R^{19}$;
$R^{25}$ represents $R^{19}$, $R^{20}SO_2$— or an acyl group —$C(O)R^{21}$.

18. A compound of formula VIII

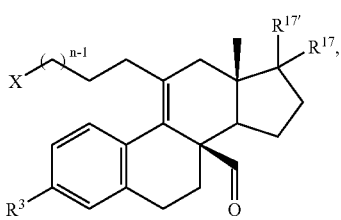

in which
$R^3$ represents a group $R^{19}$—O—, $R^{20}SO_2$—O—, or —O—$C(O)R^{21}$;
n represents 3, 4, or 5:
X represents a group of formula II

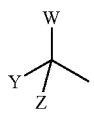

in which
Z and W, independently of one another, represent $R^{19}$,
or
Z and W together represent an oxygen atom,
Y represents $OR^{19}$, —CN, —SCN, a halogen atom, $R^{20}$, $R^{20}SO_2SO_2$—O—;
or
Y represents $R^{19}$ or $R^{20}$, if Z and W together represent an oxygen atom;
$R^{17}$ and $R^{17'}$ together represent an oxygen atom, or a group =$CR^{23}R^{24}$,
in which
$R^{23}$ and $R^{24}$, independently of one another, represent a hydrogen atom or a halogen;
or
$R^{17}$ represents hydrogen, —$OR^{19}$ or halogen;
$R^{17'}$ represents $R^{19}$, —$OR^{19}$, halogen, $R^{20}SO_2$—O—, —$C(O)R^{21}$ or —O—$C(O)R^{21}$;

$R^{19}$ represents a hydrogen atom,
a radical of formula $C_pF_qH_r$ with p=1, 2, 3, 4, 5, 6, 7, 8, 9: q>1 and q+r=2p+1;
an unbranched $C_1$-$C_8$-alkyl group or branched $C_1$-$C_6$-alkyl group, a $C_3$-$C_6$-cycloalkyl group that is optionally substituted with a phenyl radical, a ($C_3$-$C_6$-cycloalkyl)-$C_1$-$C_4$-alkylene group, a branched or unbranched $C_2$-$C_5$-alkenyl group, a $C_2$-$C_5$-alkinyl group; or an unsubstituted or substituted aryl-, heteroaryl-, heterocyclyl-, aryl-$C_1$-$C_4$-alkylene-, or heteroaryl-$C_{1-4}$-alkylene group;
$R^{20}$ represents an $R^{21}R^{22}N$— group, a group —$C(NOR^{19})$H, or a group of formula III

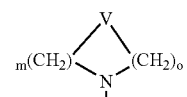

in which
V represents —$CH_2$—, an oxygen atom or a sulfur atom, or =N—$R^{25}$;
m represents 0, 1, 2, 3, 4, 5, 6, 7 or 8,
o represents 0, 1, 2, 3, 4, 5, 6, 7 or 8,
whereby their sum
m+o is 2, 3, 4, 5, 6, 7, 8, 9, 10, 11, 12;
$R^{21}$ and $R^{22}$, independently of one another, represent $R^{19}$;
$R^{25}$ represents $R^{19}$, $R^{20}SO_2$— or an acyl group —$C(O)R^{21}$.

19. A compound of formula IX

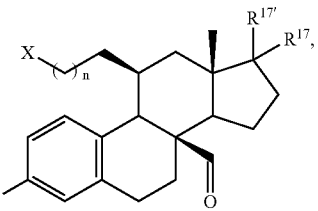

in which
$R^3$ represents a group $R^{19}$—O—, $R^{20}SO_2$—O—, or —O—$C(O)R^{21}$;
n represents 3, 4, or 5:
X represents a group of formula II

in which
Z and W, independently of one another, represent $R^{19}$,
or
Z and W together represent an oxygen atom,
Y represents $OR^{19}$, —CN, —SCN, a halogen atom, $R^{20}$, $R^{20}SO_2$—O—;
or
Y represents $R^{19}$ or $R^{20}$, if Z and W together represent an oxygen atom;

R¹⁷ and R¹⁷' together represent an oxygen atom, or a group =CR²³R²⁴, in which

R²³ and R²⁴, independently of one another, represent a hydrogen atom or a halogen;

or

R¹⁷ represents hydrogen, —OR¹⁹ or halogen;

R¹⁷' represents R¹⁹, —OR¹⁹, halogen, R²⁰SO₂—O—, —C(O)R²¹ or —O—C(O)R²¹;

R¹⁹ represents a hydrogen atom,
a radical of formula $C_pF_qH_r$ with p=1, 2, 3, 4, 5, 6, 7, 8, 9; q>1 and q+r=2p+1;
an unbranched $C_1$-$C_8$-alkyl group or branched $C_1$-$C_6$-alkyl group, a $C_3$-$C_6$-cycloalkyl group that is optionally substituted with a phenyl radical, a ($C_1$-$C_6$-cycloalkyl)-$C_1$-$C_4$-alkylene group, a branched or unbranched $C_2$-$C_5$-alkenyl group, a $C_2$-$C_5$-alkinyl group; or an unsubstituted or substituted aryl-, heteroaryl-, heterocyclyl-, aryl-$C_1$-$C_4$-alkylene-, or heteroaryl-$C_1$-$C_4$-alkylene group;

R²⁰ represents an R²¹R²²N— group, a group —C(NOR¹⁹)H, or a group of formula III

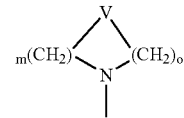

in which

V represents —CH₂—, an oxygen atom or a sulfur atom, or —N(R²⁵)—;

m represents 0, 1, 2, 3, 4, 5, 6, 7 or 8;

o represents 0, 1, 2, 3, 4, 5, 6, 7 or 8, whereby their sum m+o is 2, 3, 4, 5, 6, 7, 8, 9, 10, 11, 12;

R²¹ and R²², independently of one another, represent R¹⁹;

R²⁵ represents R¹⁹, R²⁰SO₂— or an acyl group —C(O)R²¹.

* * * * *

UNITED STATES PATENT AND TRADEMARK OFFICE
CERTIFICATE OF CORRECTION

PATENT NO.       : 7,375,098 B2                                              Page 1 of 1
APPLICATION NO.  : 10/829390
DATED            : May 20, 2008
INVENTOR(S)      : Braeuer et al.

It is certified that error appears in the above-identified patent and that said Letters Patent is hereby corrected as shown below:

Column 51, line 25 reads "11β-[(R)7,7,6-Trifluoro-6-hydroxyhept-7-enyl]-8-vinyl-es-"
should read -- 11β-[(R)7,7,6-Trifluoro-5-hydroxyhept-6-enyl]-8-vinyl-es --

Column 53, line 51 reads "ally substituted with a phenyl radical, a ($C_1$-$C_6$-"
should read -- ally substituted with a phenyl radical, a ($C_3$-$C_6$- --

Column 57, line 13 reads "an unbranched $C_1$-$C_8$-alkyl group or branched $C_1$-$C_6$-"
should read -- an unbranched $C_1$-$C_8$-alkyl group or branched $C_3$-$C_6$- --

Signed and Sealed this
Thirteenth Day of November, 2012

David J. Kappos
*Director of the United States Patent and Trademark Office*